US007381542B2

(12) United States Patent
Bunzow et al.

(10) Patent No.: US 7,381,542 B2
(45) Date of Patent: Jun. 3, 2008

(54) NUCLEIC ACIDS ENCODING A BIOGENIC AMINE RECEPTOR

(75) Inventors: James Bunzow, Portland, OR (US); David K. Grandy, Portland, OR (US); Mark Sonders, Portland, OR (US)

(73) Assignee: Oregon Health & Science University, Portland, OR (US)

(*) Notice: Subject to any disclaimer, the term of this patent is extended or adjusted under 35 U.S.C. 154(b) by 669 days.

(21) Appl. No.: 10/380,614

(22) PCT Filed: Dec. 19, 2001

(86) PCT No.: PCT/US01/28455

§ 371 (c)(1),
(2), (4) Date: Aug. 4, 2003

(87) PCT Pub. No.: WO02/22801

PCT Pub. Date: Mar. 21, 2002

(65) Prior Publication Data
US 2004/0072187 A1    Apr. 15, 2004

Related U.S. Application Data

(60) Provisional application No. 60/303,967, filed on Jul. 9, 2001.

(51) Int. Cl.
| C12N 15/00 | (2006.01) |
| C12N 15/85 | (2006.01) |
| C12N 15/63 | (2006.01) |
| C07H 21/04 | (2006.01) |
| C07K 14/00 | (2006.01) |
| C12N 1/21  | (2006.01) |

(52) U.S. Cl. .................. 435/69.1; 435/325; 435/320.1; 435/252.3; 536/23.1; 536/23.5; 536/24.31; 530/350

(58) Field of Classification Search ...................... None
See application file for complete search history.

(56) References Cited

U.S. PATENT DOCUMENTS

| 5,422,265 A | 6/1995 | Civelli et al. |
| 5,427,942 A | 6/1995 | Civelli et al. |
| 5,569,601 A | 10/1996 | Civelli et al. |
| 5,594,108 A | 1/1997 | Civelli et al. |
| 5,686,573 A | 11/1997 | Civelli et al. |
| 5,880,260 A | 3/1999 | Civelli et al. |
| 5,883,226 A | 3/1999 | Civelli et al. |

FOREIGN PATENT DOCUMENTS

| EP | 0 859 055 A | 8/1998 |
| WO | WO 00 73449 A | 12/2000 |
| WO | WO 01 36473 A | 5/2001 |
| WO | WO 01 72841 A | 10/2001 |
| WO | PCT/EP2005/007187 | 7/2005 |

OTHER PUBLICATIONS

Skolnick et al., 2000, Trends in Biotech. 18:34-39.*
Bork, P., 2000, Genome Research 10:398-400.*
Doerks et al., 1998, Trends in Genetics 14: 248-250.*
Smith et al., 1997, Nature Biotechnology 15:1222-1223.*
Ji, et al, 1998, JBC, 273:17299.*
Brenner, 1999, Trends in Genetics 15:132-133.*
Bork et al., 1996, Trends in Genetics 12:425-427.*
Padbury, et al, 1997, Mol. Brain Res., 45: 163-168.*
Gerald, et al, 1995, EMBO J. 14: 2806-2815.*
Amlaiky and Caron, "Identification of the $D_2$-Dopamine Receptor Binding Subunit in Several Mammalian Tissues and Species by Photoaffinity Labeling," *J. Neurochem.* 47, 196-204 (1986).
Amlaiky and Caron, "Photoaffinity Labeling of the $D_2$-dopamine Receptor Using a Novel High Affinity Radioiodinated Probe," *J. Biol Chem.* 260, 1983-1986 (1985).
Amlaiky et al., "Identification of the Binding Subunit of the $D_1$-Dopamine Receptor by Photoaffinity Crossliking," *Mol. Pharmacol.* 31, 129-134 (1987).
Bunzow et al., "Cloning and expression of the rat $D_2$ dopamine receptor cDNA," *Nature* 336, 783-787 (1988).
Chirgwin et al., "Isolation of Biologically Active Ribonucleic Acid from Sources Enriched in Ribonuclease," 1979, Biochemistry 5294-5299.
Cooper et al., "Catecholamines II: CNS Aspects," in *The Biochemical Basis of Neuropharmacology*, 3d ed. 1978 (Oxford University Press, N.Y.), pp. 161-195.
Civelli et al., "Molecular Diversity of the Dopamine Receptors" *Ann. Rev. Pharmacol. Toxicol.* 32:281-307 (1993).
Cotecchia et al., "Molecular cloning and expression of the cDNA for the hamster $\alpha_1$-adrenergic receptor" *Proc. Natl. Acad. Sci.*, 85:7159-63.
Dal Toso et al. "The Dopamine $D_2$ receptor: two molecular forms generated by alternative splicing" *EMBO J.* 8:4025-34 (1989).

(Continued)

*Primary Examiner*—Elizabeth C. Kemmerer
*Assistant Examiner*—Sandra Wegert
(74) *Attorney, Agent, or Firm*—Jagtiani + Guttag

(57) ABSTRACT

The present invention relates to novel mammalian biogenic amine receptor proteins and genes that encode such proteins. The invention is directed toward the isolation and characterization of mammalian trace amine receptor proteins. The invention specifically provides isolated complementary DNA copies of mRNA corresponding to rat and human homologues of a mammalian trace amine receptor gene. Also provided are recombinant expression constructs capable of expressing the mammalian trace amine receptor genes of the invention in cultures of transformed prokaryotic and eukaryotic cells, as well as such cultures of transformed cells that synthesize the mammalian trace amine receptor proteins encoded therein. The invention also provides methods for screening compounds in vitro that are capable of binding to the mammalian trace amine receptor proteins of the invention, and further characterizing the binding properties of such compounds and functional consequences thereof in comparison with known trace amine receptor agonists and antagonists. Improved methods of pharmacological screening are provided thereby.

9 Claims, 23 Drawing Sheets

OTHER PUBLICATIONS

Dixon et al., "Cloning of the gene and cDNA for mammalian β-adrenergic receptor and homology with rhodopsin" *Nature* 321:75-79 (1986).

Dixon et al., Annual Reports in Medicinal Chemistry, 23: 221-233.

Eisenberg et al., "Analysis of Membrane and Surface Protein Sequences with the hydrophobic Moment Plot", *J. Mol. Biol.* 179:125-142 (1984).

Emorine et al., "Structure of the gene for human β$_2$-adrenergic receptor:Expression and promoter characterization" Proc. Natl. Acad. Sci. 84:6995-6999 (1987).

Frielle et al., "Cloning of the cDNA for the human β$_1$-adrenergic receptor" *Proc. Natl. Acad. Sci.* (1987) 34:7920-7924.

Gingrich et al., *J Biochemistry* 27, 3907-3912 (1988).

Grandy et al., "Cloning of the cDNA and gene for a human D$_2$ dopamine receptor," *Proc. Natl. Acad. Sci. USA* 86:9762-9766 (1989).

Hoffman et al., "Adrenergic Receptors in the Heart" *Ann Rev. Physiol.* 1982 44:475-84.

Jarvie et al., "Dopamine D$_2$ Receptor Binding Subunits of M$_r$≅140,000 and 94,000 in Brain: Deglycosylation Yields a Common Unit of M$_r$≅44,000," *Mol. Pharmacol.* 34:91-97 (1988).

Kebabian and Calne, "Multiple receptors for dopamine," *Nature* 277:93-96 (1979).

Kobilka, "Cloning, Sequencing, and Expression of the Gene Coding for the Human Platelet α$_{2\text{-Adrenergic}}$ Receptor" B.K. *Science* 238:650-656 (1987).

Probst et al., "Sequence Alignment of the G-Protein Coupled Receptor Superfamily" *DNA and Cell Biology* 11(1)1-20 (1990).

Saiki et al., "Primer-Directed Enzymatic Amplification of DNA with a Thermostable DNA Polymerase" *Science* 239:487-491.

Sanger et al., "DNA sequencing with chain-terminating inhibitors," *Proc. Natl. Acad. Sci. USA* 74(12) 5463-5467 (1977).

Seeman, "Dopamine Receptors and the Dopamine Hypothesis of Schizophrenia" *Synapse* 1:133-152 (1987).

Sengoles et al., "Purification and Characterization of the D$_2$-Dopamine Receptor from Bovine Anterior Pituitary," *J. Biol. Chem.* 263:18996-19002 (1988).

Senogles et al., "Affinity Chromatography of the Anterior Pituitary D$_2$-Dopamine Receptor" *American Chemical Society* 25:749-753 (1986).

Smithies et al., "Insertion of DNA sequences into the human chromosomal β-globin locus by homologus recombination," *Nature* 317:230-234 (1985).

Sokoloff et al., "Molecular cloning and characterization of a novel dopamine receptor (D$_3$) as a target for neuroleptics," *Nature* 347:146-151 (1990).

Sunahara et al., "Human dopamine D$_1$ receptor encoded by an intronless gene on chromosome 5," *Nature* 347:80-83 (1990).

Van Tol et al., "Cloning of the gene for a human dopamine D4 receptor with high affinity for the antipsychotic clozapine," *Nature* 350:610-614 (1991).

Zhou et al., "Cloning and expression of human and rad D$_1$ dopamine receptors," *Nature* 347:76-80 (1990).

Bunzow et al., "Amphetamine 3, 4-Methylenedioxymethamphetamine, lysergic acid diethylamide, and metabolites of the catecholamine neurotransmitters are agonists of a rat trace amine receptor," *Molecular Pharmacology.* 60(6):1181-88 (Dec. 2001).

Borowsky et al., "Trace amines: identification of a family of a mammalian G protein-coupled receptors," *Proc. Of the Nat. Acad. Of Sci. of USA* 98(16):8966-71 (Jul. 31, 2001).

Lee et al., "Cloning and Characterization of Additional Members of the G Protein-Coupled Receptor Family," *Biochimica et Biophysica Acta.* 1490(2000):311-23.

Zeng et al., "Cloning of a putative human neurotransmitter receptor expressed in skeletal muscle and brain," *Biochemical and Biophysical Research Communications.* 242(3):575-78 (1998).

Singewald et al., "Involvement of biogenic amines and amino acids in the central regulation of cardiovascular homeostasis," *Trends in Pharmacological Sciences.* 17(10):356-63 (1996).

Szikra et al., "Receptor Binding Properties of Hemorphin Analogue in Rat Brain Membrane Preparations," *Neurobiology.* 4(3):279-80 (1996).

* cited by examiner

Figure 1

```
              10         20          29         38         47         56
                          >
CTAATTGACA GCCCTCAGGA ATG ATG CCC TTT TGC CAC AAT ATA ATT AAT ATT TCC
                      MET MET Pro Phe Cys His Asn Ile Ile Asn Ile Ser 65         74          83         92        101        110
TGT GTG AAA AAC AAC TGG TCA AAT GAT GTC CGT GCT TCC CTG TAC AGT TTA ATG
Cys Val Lys Asn Asn Trp Ser Asn Asp Val Arg Ala Ser Leu Tyr Ser Leu MET 119        128         137        146        155        164
GTG CTC ATA ATT CTG ACC ACA CTC GTT GGC AAT CTG ATA GTT ATT GTT TCT ATA
Val Leu Ile Ile Leu Thr Thr Leu Val Gly Asn Leu Ile Val Ile Val Ser Ile 173        182         191        200        209        218
TCA CAC TTC AAA CAA CTT CAT ACC CCA ACA AAT TGG CTC ATT CAT TCC ATG GCC
Ser His Phe Lys Gln Leu His Thr Pro Thr Asn Trp Leu Ile His Ser MET Ala 227        236         245        254        263        272
ACT GTG GAC TTT CTT CTG GGG TGT CTG GTC ATG CCT TAC AGT ATG GTG AGA TCT
Thr Val Asp Phe Leu Leu Gly Cys Leu Val MET Pro Tyr Ser MET Val Arg Ser 281        290         299        308        317        326
GCT GAG CAC TGT TGG TAT TTT GGA GAA GTC TTC TGT AAA ATT CAC ACA AGC ACC
Ala Glu His Cys Trp Tyr Phe Gly Glu Val Phe Cys Lys Ile His Thr Ser Thr 335        344         353        362        371        380
GAC ATT ATG CTG AGC TCA GCC TCC ATT TTC CAT TTG TCT TTC ATC TCC ATT GAC
Asp Ile MET Leu Ser Ser Ala Ser Ile Phe His Leu Ser Phe Ile Ser Ile Asp 389        398         407        416        425        434
CGC TAC TAT GCT GTG TGT GAT CCA CTG AGA TAT AAA GCC AAG ATG AAT ATC TTG
Arg Tyr Tyr Ala Val Cys Asp Pro Leu Arg Tyr Lys Ala Lys MET Asn Ile Leu 443        452         461        470        479        488
GTT ATT TGT GTG ATG ATC TTC ATT AGT TGG AGT GTC CCT GCT GTT TTT GCA TTT
Val Ile Cys Val MET Ile Phe Ile Ser Trp Ser Val Pro Ala Val Phe Ala Phe 497        506         515        524        533        542
GGA ATG ATC TTT CTG GAG CTA AAC TTC AAA GGC GCT GAA GAG ATA TAT TAC AAA
Gly MET Ile Phe Leu Glu Leu Asn Phe Lys Gly Ala Glu Glu Ile Tyr Tyr Lys 551        560         569        578        587        596
CAT GTT CAC TGC AGA GGA GGT TGC TCT GTC TTC TTT AGC AAA ATA TCT GGG GTA
His Val His Cys Arg Gly Gly Cys Ser Val Phe Phe Ser Lys Ile Ser Gly Val 605        614         623        632        641        650
CTG ACC TTT ATG ACT TCT TTT TAT ATA CCT GGA TCT ATT ATG TTA TGT GTC TAT
Leu Thr Phe MET Thr Ser Phe Tyr Ile Pro Gly Ser Ile MET Leu Cys Val Tyr
```

```
        659         668         677         686         695         704
TAC AGA ATA TAT CTT ATC GCT AAA GAA CAG GCA AGA TTA ATT AGT GAT GCC AAT
Tyr Arg Ile Tyr Leu Ile Ala Lys Glu Gln Ala Arg Leu Ile Ser Asp Ala Asn 713         722         731         740         749         758
CAG AAG CTC CAA ATT GGA TTG GAA ATG AAA AAT GGA ATT TCA CAA AGC AAA GAA
Gln Lys Leu Gln Ile Gly Leu Glu MET Lys Asn Gly Ile Ser Gln Ser Lys Glu 767         776         785         794         803         812
AGG AAA GCT GTG AAG ACA TTG GGG ATT GTG ATG GGA GTT TTC CTA ATA TGC TGG
Arg Lys Ala Val Lys Thr Leu Gly Ile Val MET Gly Val Phe Leu Ile Cys Trp 821         830         839         848         857         866
TGC CCT TTC TTT ATC TGT ACA GTC ATG GAC CCT TTT CTT CAC TAC ATT ATT CCA
Cys Pro Phe Phe Ile Cys Thr Val MET Asp Pro Phe Leu His Tyr Ile Ile Pro 875         884         893         902         911         920
CCT ACT TTG AAT GAT GTA TTG ATT TGG TTT GGC TAC TTG AAC TCT ACA TTT AAT
Pro Thr Leu Asn Asp Val Leu Ile Trp Phe Gly Tyr Leu Asn Ser Thr Phe Asn 929         938         947         956         965         974
CCA ATG GTT TAT GCA TTT TTC TAT CCT TGG TTT AGA AAA GCA CTG AAG ATG ATG
Pro MET Val Tyr Ala Phe Phe Tyr Pro Trp Phe Arg Lys Ala Leu Lys MET MET 983         992         1001        1010        1019        1028
CTG TTT GGT AAA ATT TTC CAA AAA GAT TCA TCC AGG TGT AAA TTA TTT TTG GAA
Leu Phe Gly Lys Ile Phe Gln Lys Asp Ser Ser Arg Cys Lys Leu Phe Leu Glu

1037  ─>      1050        1060        1070        1080        1090
TTG AGT TCA TAG AATTATTATA TTTTACTGTT TTGCAAATCG GTTGATGATC ATATTTATGA
Leu Ser Ser 1100        1110        1120
ACACAACATA ACGAACCACA TGCACCAACC ACATG
```

```
                                    27                                              54
ATG CAT CTT TGC CAC AAT AGC GCG AAT ATT TCC CAC ACG AAC AGG AAC TGG TCA
MET His Leu Cys His Asn Ser Ala Asn Ile Ser His Thr Asn Arg Asn Trp Ser 81                                             108
AGG GAT GTC CGT GCT TCA CTG TAC AGC TTA ATA TCA CTC ATA ATT CTA ACC ACT
Arg Asp Val Arg Ala Ser Leu Tyr Ser Leu Ile Ser Leu Ile Ile Leu Thr Thr 135                                             162
CTG GTT GGC AAC TTA ATA GTA ATC ATT TCG ATA TCC CAC TTC AAG CAA CTT CAC
Leu Val Gly Asn Leu Ile Val Ile Ile Ser Ile Ser His Phe Lys Gln Leu His 189                                             216
ACG CCC ACA AAT TGG CTC CTT CAT TCC ATG GCC GTT GTC GAC TTT CTG CTG GGC
Thr Pro Thr Asn Trp Leu Leu His Ser MET Ala Val Val Asp Phe Leu Leu Gly 243                                             270
TGT CTG GTC ATG CCC TAC AGC ATG GTG AGA ACA GTT GAG CAC TGC TGG TAC TTT
Cys Leu Val MET Pro Tyr Ser MET Val Arg Thr Val Glu His Cys Trp Tyr Phe 297                                             324
GGG GAA CTC TTC TGC AAA CTT CAC ACC AGC ACT GAT ATC ATG CTG AGC TCG GCA
Gly Glu Leu Phe Cys Lys Leu His Thr Ser Thr Asp Ile MET Leu Ser Ser Ala 351                                             378
TCC ATT CTC CAC CTA GCC TTC ATT TCC ATT GAC CGC TAC TAT GCT GTG TGC GAC
Ser Ile Leu His Leu Ala Phe Ile Ser Ile Asp Arg Tyr Tyr Ala Val Cys Asp 405                                             432
CCT TTA AGA TAC AAA GCC AAG ATC AAT CTC GCC GCC ATT TTT GTG ATG ATC CTC
Pro Leu Arg Tyr Lys Ala Lys Ile Asn Leu Ala Ala Ile Phe Val MET Ile Leu 459                                             486
ATT AGC TGG AGC CTT CCT GCT GTT TTT GCA TTT GGG ATG ATC TTC CTG GAG CTG
Ile Ser Trp Ser Leu Pro Ala Val Phe Ala Phe Gly MET Ile Phe Leu Glu Leu 513                                             540
AAC TTA GAA GGA GTT GAG GAG CAG TAT CAC AAT CAG GTC TTC TGC CTG CGC GGC
Asn Leu Glu Gly Val Glu Glu Gln Tyr His Asn Gln Val Phe Cys Leu Arg Gly 567                                             594
TGT TTT CTA TTC TTC AGT AAA GTA TCT GGG GTA CTG GCA TTC ATG ACG TCT TTC
Cys Phe Leu Phe Phe Ser Lys Val Ser Gly Val Leu Ala Phe MET Thr Ser Phe 621                                             648
TAT ATA CCT GGG TCT GTT ATG TTA TTT GTT TAC TAT AGA ATA TAT TTC ATA GCT
Tyr Ile Pro Gly Ser Val MET Leu Phe Val Tyr Tyr Arg Ile Tyr Phe Ile Ala
```

```
                                    675                                              702
AAA GGA CAA GCG AGG TCA ATT AAT CGT GCA AAC CTT CAA GTT GGA TTG GAA GGG
Lys Gly Gln Ala Arg Ser Ile Asn Arg Ala Asn Leu Gln Val Gly Leu Glu Gly 729                                              756
GAA AGC AGA GCG CCA CAA AGC AAG GAA ACA AAA GCC GCG AAA ACC TTA GGG ATC
Glu Ser Arg Ala Pro Gln Ser Lys Glu Thr Lys Ala Ala Lys Thr Leu Gly Ile 783                                              810
ATG GTG GGC GTT TTC CTC CTG TGC TGG TGC CCG TTC TTT TTC TGC ATG GTC CTG
MET Val Gly Val Phe Leu Leu Cys Trp Cys Pro Phe Phe Phe Cys MET Val Leu 837                                              864
GAC CCT TTC CTG GGC TAT GTT ATC CCA CCC ACT CTG AAT GAC ACA CTG AAT TGG
Asp Pro Phe Leu Gly Tyr Val Ile Pro Pro Thr Leu Asn Asp Thr Leu Asn Trp 891                                              918
TTC GGG TAC CTG AAC TCT GCC TTC AAC CCG ATG GTT TAT GCC TTT TTC TAT CCC
Phe Gly Tyr Leu Asn Ser Ala Phe Asn Pro MET Val Tyr Ala Phe Phe Tyr Pro 945                                              972
TGG TTC AGA AGA GCG TTG AAG ATG GTT CTC TTC GGT AAA ATT TTC CAA AAA GAT
Trp Phe Arg Arg Ala Leu Lys MET Val Leu Phe Gly Lys Ile Phe Gln Lys Asp

999
TCA TCT AGG TCT AAG TTA TTT TTG TAA
Ser Ser Arg Ser Lys Leu Phe Leu
```

Figure 2 (cont'd.)

```
rTAR         ------MHLCHNSANISHTNSNWSRDVRASLYSLISLIILT-------TLVGNLIVIISI
hTAR         -----MMPFCHNIINISCVKNNWSNDVRASLYSLMVLIILT-------TLVGNLIVIVSI
GPCR57       ----MDLTYIPEDLSSCPKFVNKILSSHQPLFSCPGDNVFGYDWSHDYPLFGNLVIMVSI
GPCR58       --------------------------MYSFMAGSIF-------ITIFGNLAMIISI
NT Receptor  -MRAVFIQGAEEHPAAFCYQVNGSCPRTVHTLGIQLVIYLTCAAGMLIIVLGNVPVAFAV
r5ht4R       -------MDRLDANVSSNEGFGSVEKVVLLTPFAMVILM--------AILGNLLVMVAV
hD1R         -----MRTLNTSAMDGTGLVVERDFSVRILTACFLSLLILS-------TLLGNTLVCAAV
hB2R         MGQPGNGSAFLLAPNGSHAPDHDVTQQRDEVWVVGMGIVMS--LIVLAIVFGNVLVITAI rTAR         SHFKQLH-TPTNWLLHSMAVVDFLLGCLVMPYSMVRTVEHCWYFGELFCKLHTSTDIMLS
hTAR         SHFKQLH-TPTNWLIHSMATVDFLLGCLVMPYSMVRSAEHCWYFGEVFCKIIITSTDIMLS
GPCR57       SHFKQLH-SPTNFLILSMATTDFLLGFVIMPYSIMRSVESCWYFGDGFCKFHTSFDMMLR
GPCR58       SYFKQLH-TPTNFLILSMAITDFLLGFTIMPYSMIRSVENCWYFGLTFCKIYYSFDLMLS
NT Receptor  SYFKALH-TPTNFLLLSLALADMFLGLLVLPLSTIRSVESCWFFGDFLCRLHTYLDTLFC
r5ht4R       CDRDRQLRKIKTNYFIVSLAFADLLVSVLVNAFGALELVQDIWFYGEMFCLVRTSLDVLLT
hD1R         IRERHLRSKVTNFFVISLAVSDLLVAVLVMPWKAVAEIAGFWPFGS-FCNIWVAFDIMCS
hB2R         AKFERLQ-TVTNYFITSLACADLVMGLAVVPFGAAHILMKMWTFGNFWCEFWTSIDVLCV rTAR         SASILHLAFISIDRYYAVC-DPLRVKAKINLAAIFVMLISWSLPAVFAFGMIFL----E
hTAR         SASIFHLSFISIDRYYAVC-DPLRVKAKMNILVICVMFISWSVPAVFAFGMIFL----E
GPCR57       LTSIFHLCSIAIDRFYAVC-YPLHYTTKMTNSTIKQLLAFCWSVPALFSFGLVLS---E
GPCR58       ITSIFHLCSVAIDRFYAIC-YPLLYSTKIIPVIKRLLLLCWSVPGAFAFGAVFS---E
NT Receptor  LTSIFHLCFISIDRHCAIC-DPLLYPSKFTRVALRYILAGWGVPAAYTSLFLYT----D
r5ht4R       TASIFHLCCISLDRYYAICCQPLVVRNKMTPLRIALMLGGCWVIPMFISTLPIMQGWNNI
hD1R         TASILNLCVISVDRYWAIS-SPFRYERKMTPKAAFILISVAWTLSVLISFIPVQLSWHKA
hB2R         TASIETLCVIAVDRYFAIT-SPFKYQSLLTKNKARVIILMVWIVSGLTSFLPIQM---- rTAR         LNLEGVEEQVHNQVFCLRGCFPFFSKVSGVLAFMTSFYIPGSVMLFVYYRIYPIAKGQAR
hTAR         LNFKGAEEIVYKHVHCRGGCSVFFSKISGVLTPMTSFYIPGSIMLCVYYRIYLIAKEQAR
GPCR57       ADVSGMQS-YKILVACFNFCALTFNKFWGTILFTTCFFTPGSIMVGIYGKIFIVSKQHAR
GPCR58       AYADGIEG-YDILVACSSSCPVMFNKLWGTTLFMAGFFTPGSMMVGIYGKIFAVSRKHAH
NT Receptor  VVETRLSQ-WLEEMPCVGSCQLLLNKFWGWLNFP-LFFVPCLIMISLYVKIFVVATRQAQ
r5ht4R       GIVDVIEKRKFNHNSNSTPCVFMVNKPYAIITCSVVAFYIPFLLMVLAYYRIYVTAKEHAQ
hD1R         KPTSPSDGNATSLAETIDNCDSSLSRTYAISSSVISFYIPVAIMIVTYTRIYRIAQKQIR
hB2R         HWYRATHQEAINCYANETCCDFFTNQAYAIASSIVSFYVPLVIMVFVYSRVFQEAKRQLQ rTAR         SINRAN---------LQVGLEGESRAPQS---------KETKAAKTLGIMVGVFLLCW
hTAR         LISDANQK--------LQIGLEMKNGISQS---------KERKAVKTLGIVMGVFLTCW
GPCR57       VISHVP---------ENTKGAVKKHLSKK----------KDRKAAKTLGIVMGVFLACW
GPCR58       AINNLR---------ENQNNQVK-----------------KDKKAAKTLGIVTGVFLLCW
NT Receptor  QITTLS---------KSLAGAAK-----------------HERKAAKTLGIVVGIYLLCW
r5ht4R       QIQMLQRA-------GATSESRPQTADCHST----HRMRTETKAAKTLCVIMGCFCFCW
hD1R         RIAALERAAVHAKNCQTTTGNGKPVECSQPESSFK-MSFKRETKVLKTLSVIMGVFVCCW
hB2R         KIDKSEGR-----FHVQNLSQVBQDGRTGHGLRRSSKFCLKEHKALKTLGIIMGTFTLCW rTAR         CPFFFCMVLDPFLG------VVIPPTLNDTLNWFGYLNSAFNPMVYAFFYPWRRALKMV
hTAR         CPFFICTVMDPFLH------VIIPPTLNDVLIWFGYLNSTFNPMVYAFFYPWRKALKMM
GPCR57       LPCFLAVLIDPYLD------YSTPILILDLLWLRYFNSTCNPLIHGFFNPWFQKAFKYI
GPCR58       FPCFFTILLDPFLN------FSTPVVLFDALTWFGYFNSTCNPLIYGFFYPWFRRALKYI
NT Receptor  LPFTIDTMVDSLLH------FITPPLVFDIFIWFAYFNSACNPILYVFSMQWFRKALKLT
r5ht4R       APFFVTNIVDPFID------YTVEKVWTAFLWLGYINSGLNPFLYAFLNKSFRRAFLII
hD1R         LPFFILNCILPFCGSGETQPFCIDSNTFDVFVWFGWANSSLNPIIYAFN-ADFRKAFSTL
hB2R         LPFFIVNIVHVIQD-----NLIRKEVYILLNWIGYVNSGFNPLIYCRS-PDFRIAFQEL rTAR         LFGKIFQK--DSSRSKLFL---------------------------
hTAR         LFGKIFQK--DSSRCKLFLELSS------------------------
GPCR57       VSGKIFSS--HSETANLFPEAH-------------------------
GPCR58       LLGKIFSSCFHNTILCMQKESE-------------------------
NT Receptor  LSQKVFSP--QTRTVDLYQE---------------------------
r5ht4R       LCCDDERYKRPPILGQTVPCSTTTINGSTHVLRD---TVECGGQWESRCHLTATS-----
hD1R         LGCYRLCPATNNAIETVSINNNGAAMFSSHHEPRGSISKECNLVYLIPHAVGSSEDLKKE
hB2R         LCLRRSSL--KAYGNGYSSNGNTGEQSGYHVEQEKENKLLCEDLPGTEDFVGHQG----- rTAR         -------------------
hTAR         -------------------
GPCR57       -------------------
GPCR58       -------------------
NT Receptor  -------------------
r5ht4R       -------PLVAAQPVIRRPQDNDLEDSCSLKRSQS-----
hD1R         EAAGIARPLEKLSPALSVILDYDTDVSLEKIQPITQNGQL...
hB2R         --------TVPSDNIDSQGRNCSTNDSLL-----------
```

Fig. 3

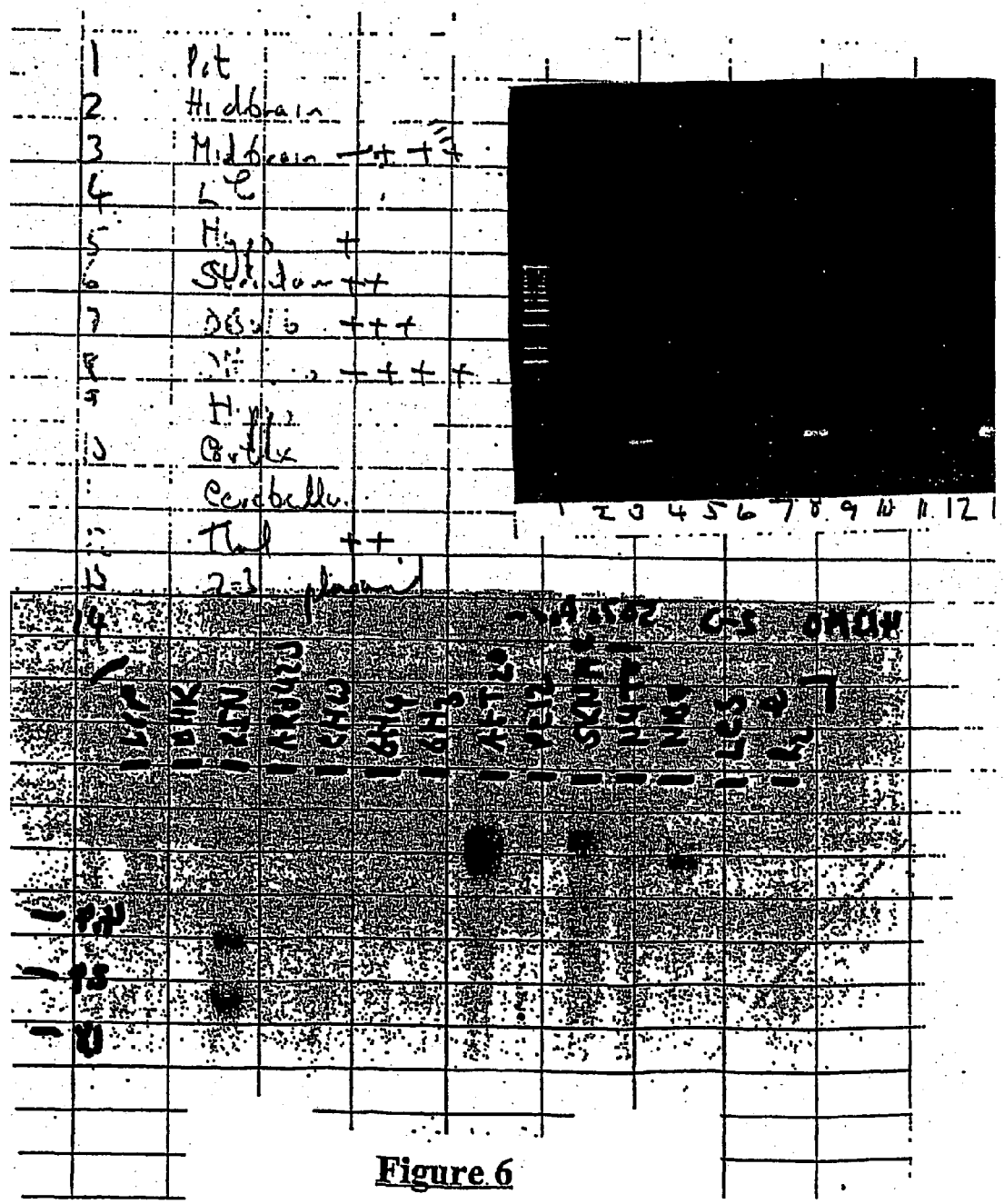

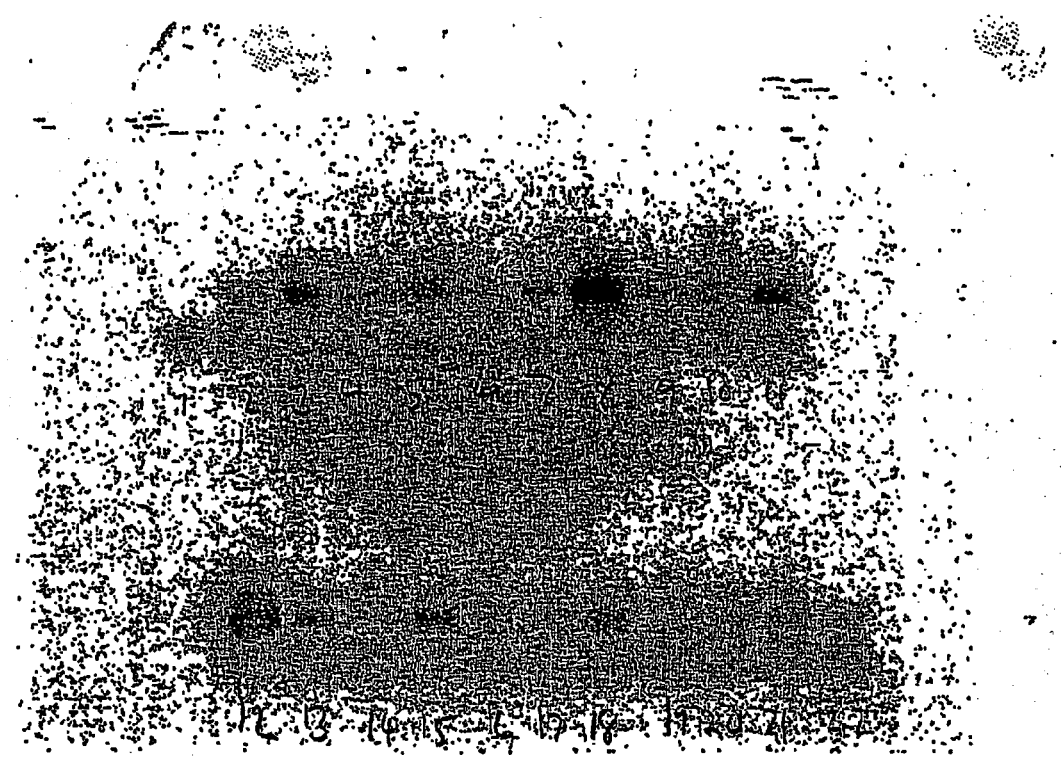
Figure 8B
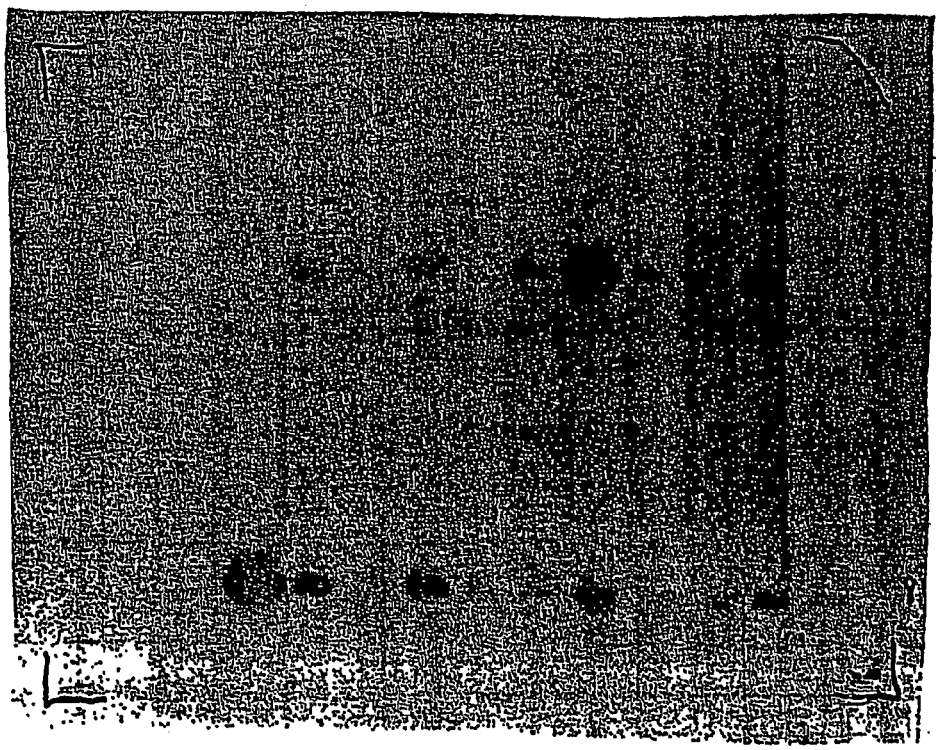

NUCLEIC ACIDS ENCODING A BIOGENIC AMINE RECEPTOR

This application is a U.S. national phase application pursuant to 35 U.S.C. §371 of International Application No. PCT/US01/28455, filed 12 Sep. 2001, which claims priority to U.S. patent application Ser. No. 09/659,529, filed Jul. 9, 2001, now U.S. Pat. No. 6,783,973 and U.S. Provisional Patent Application, Ser. No. 60/303,967, filed Sep. 12, 2000, the disclosures of each of which are incorporated herein by reference.

This invention was made with government support under National Institute of Health grants DA08562. The government has certain rights to this invention.

BACKGROUND OF THE INVENTION

1. Field of the Invention

This invention relates to biogenic amine receptors from mammalian species and the genes corresponding to such receptors. Specifically, the invention relates to the isolation, cloning and sequencing of complementary DNA (cDNA) copies of messenger RNA (mRNA) encoding a novel mammalian biogenic amine receptor gene. The invention also relates to the construction of recombinant expression constructs comprising cDNA of this novel receptor gene, said recombinant expression constructs being capable of expressing receptor protein in cultures of transformed prokaryotic and eukaryotic cells. Production of the receptor protein in such cultures is also provided. The invention relates to the use of such cultures of such transformed cells to produce homogeneous compositions of the novel biogenic amine receptor protein. The invention also provides cultures of such cells producing this receptor protein for the cation of novel and useful drugs. Antibodies against and epitopes of this novel biogenic amine receptor protein are also provided by the invention

2. Background of the Invention

Biogenic amines are a class of naturally-occurring amino acid derivatives having a variety of physiological effects in the peripheral and central nervous systems. The parent compound is β-phenylethylamine, and derivatives of this compound include the biogenic amines. The biogenic amines are a large and diverse class of compounds that include dopamine, noradrenaline, epinephrine, norepinephrine, and serotonin. The biogenic amines are implicated in a variety of psychiatric and neurologic disorders.

In the periphery, biogenic amines are released by the sympathetic nervous system and adrenal medulla and are involved in integrating physiological responses to stress, while in the central nervous system the biogenic amines constitute some of the most important neurotransmitter systems.

The effects of biogenic amines are mediated through their receptors and their associated cell signaling systems (reviewed in Hoffman & Lefkowitz, 1982, *Ann Rev. Physiol.* 44: 475-484; Civelli et al., 1993, *Ann. Rev. Pharm. & Tox.* 33: 281-307). These receptors are located in the plasma membrane of biogenic amine-sensitive cells. Structurally, they are characterized by having a pattern of seven transmembrane domains (see, for example, U.S. Pat. Nos. 5,422,265, 5,569,601, 5,594,108, 5,883,226, 5,880,260, 5,427,942 and 5,686,573). Functionally, certain of these receptors interact with adenylate cyclase, either stimulating or inhibiting the production of cyclic AMP thereby. These receptors include the adrenergic receptors (the a-1, a-2, b-1, b-2, and b-3 adrenergic receptors) and the dopamine receptors (the $D_1$-, $D_2$-, $D_3$-, $D_{-4}$-, and $D_5$-dopamine receptors).

For example, epinephrine (adrenaline) and norepinephrine, as well as synthetic agonists of these biogenic amines which mimic their biological functions, and antagonists which block these biological functions, exert their effects by binding to specific recognition sites, (membrane receptors) situated on the cell membranes in the nervous system. Two principal classes of adrenergic receptors have been defined, the alpha-adrenergic receptors and the beta-adrenergic receptors. Five subtypes of adrenergic receptors (a-1, a-2, b-1, b-2, and b-3 adrenegic receptors) have now been distinguished. The genes encoding these receptors have been isolated and identified (Cotecchia et al., 1988, *Proc. Natl. Acad. Sci. USA* 85: 7159-7163; Kobilka et al., 1987, *Science* 238: 650-656; Frielle et al., 1987, *Proc. Natl. Acad. Sci. USA* 84: 7920-7924; Emorine et al., 1987, *Proc. Natl. Acad. Sci. USA* 84: 6995-6999; Eorine et al., 1989, *Science* 245: 1118-1121). Analysis of these genes has made it possible to recognize that they belong to a family of integral membrane receptors exhibiting some homology (Dixon et al., 1998, Annual Reports in Medicinal Chemistry, 221-223; Emorine et al., 1988, *Proc. NATO Adv. Res. Workshop*), especially at portions of the seven transmembrane regions that are coupled to regulatory proteins, called G proteins, capable of binding molecules of guanosine triphosphate (GTP).

These membrane receptors, after they have bound the appropriate ligand (agonist or antagonist), are understood to undergo a conformational change that induces an intracellular signal that modifies the behavior of the target cell. Beta-adrenergic receptors catalyze the activation of a class of G proteins, which in turn stimulates the activity of adenylate cyclase when they bind with biogenic amine agonists, whereas alpha-adrenergic receptor antagonists act in competition with the agonists for the binding to the receptor and prevent the activation of adenylate cyclase. When adenylate cyclase is activated, it catalyses the production of an intracellular mediator or second messenger, especially cyclic AMP.

In the central nervous system, dopamine is a biogenic amine neurotransmitter that modulates neuronal cells involved in movement initiation, appetitive behavior, hormone release, and visual dark adaptation. In the periphery dopamine plays a role in modulating blood pressure and renal function (see generally Cooper et al., 1978, THE BIOCHEMICAL BASIS OF NEUROPHARMACOLOGY, 3d ed., Oxford University Press, New York, pp, 161-195). The diverse physiological actions of dopamine are in turn mediated by its interaction with family of distinct dopamine receptors subtypes that are either "D1-like" or "D2-like," which respectively stimulate and inhibit the enzyme adenylate cyclase Kebabian & Calne, 1979, *Nature* 277: 93-96). Alterations in the number or activity of these receptors may be a contributory factor in disease states such as Parkinson's disease (a movement disorder) and schizophrenia (a behavioral disorder) and attention deficit hyperactivity disorder (ADHD).

A great deal of information has accumulated regarding the biochemistry of the D1 and D2 dopamine receptors, and methods have been developed to solubilize and purify these receptor proteins (see Senogles et, al, 1986, *Biochemistry* 25: 749-753; Sengoles et al., 1988, *J. Biol. Chem.* 263: 18996-19002; Gingrch et al., 1988, *Biochemistry* 27: 3907-3912). The D1 dopamine receptor in several tissues appears to be a glycosylated membrane protein of about 72 kD (Amlaiky et al., 1987, *Mol. Pharmacol.* 31: 129-134; Ninzik et al., 1988, *Biochemistry* 27: 7594-7599). The D2 receptor can also be glycosylated and has been suggested to have a higher molecular weight of about 90-150 kD (Amlaiky & Caron, 1985, *J. Biol. Chem.* 260: 1983-1986; Amlaiky & Caron, 1986, *J. Neurochem.* 47: 196-204; Jarvie et al., 1988, *Mol. Pharmacol.* 34: 91-97).

Dopamine receptors are primary targets in the clinical treatment of psychomotor disorders such as Parkinson's disease and affective disorders such as schizophrenia (Seeman et al., 1987, *Neuropsychopharm.* 1: 5-15; Seeman, 1987, *Synapse* 1:152-333). Five different dopamine receptor genes (1, D2, D3, D4 and D5) and various splice variants of their transcripts have been cloned as a result of nucleotide sequence homology which exists between these receptor genes (Bunzow et al., 1988, *Nature* 336: 783-787; Grandy et al., 1989, *Proc. Natl. Acad. Sci. USA* 86: 9762-9766; Dal Toso et al., 1989, *EMBO J.* 8: 4025-4034; Zhou et al., 1990, *Nature* 346: 76-80; Sunahara et al., 1990, *Nature* 346: 80-83; Sokoloff et al., 1990, *Nature* 347: 146-151; Civelli et al., 1993, *Annu. Rev. Pharmacol. Toxicol.* 33: 281-307; Van Tol et al., 1991, *Nature* 350: 610-4).

Biogenic amine receptors are also targets for a host of therapeutic agents for the treatment of shock hypertension, arrhythmias, asthma, migraine headache, and anaphylactic reactions, and include antipsychotic drugs that are used to treat schizophrenia and β-blockers used to control high blood pressure.

In addition to these compounds, a number of biogenic amines are present in much lower quantities (less than 1% of the biogenic amines) and are therefore known as trace amines. The trace amines include such compounds as para-tyramine (p-tyramine), meta-tyramine (m-tyramine), phenylethylamine, octopamine, and tryptamine. The trace amines β-phenethylamine (β-PEA), p-tyramine, tryptamine, and octopamine are found in peripheral tissues as well as the central nervous system (Tallman et al., 1976, *J Pharmacol Exp Ther* 199: 216-221; Paterson et al., 1990, *J Neurochem* 55: 1827-37). In vivo β-PEA and p-tyramine can be synthesized from phenylalanine or tyrosine by the enzyme amino acid decarboxylase. (Boulton and Dyck, 1974, *Life Sci* 14: 2497-2506; Tallman et al., 1976, ibid.).

Investigations into the effects of trace amines on smooth muscle and glandular preparations early in the twentieth century clearly demonstrated that amines produced by putrefaction and lacking the catechol nucleus were capable of producing robust sympathomimetic effects (Barger and Dale, 1910, *J Physiol* 41: 19-59). Currently it is thought that p-tyramine and β-PEA manifest their peripheral effects by promoting the efflux of catecholamines from sympathetic neurons and adrenals (Schonfeld and Trendelenburg, 1989, *Naunyn Schmiedeberg's Arch Pharmacol* 339: 433-440; Mundorf et al., 1999, *J Neurochem* 73: 2397-2405) which results in the indirect stimulation of adrenergic receptors (Black et al., 1980, *Eur J Pharmacol* 65: 1-10).

Sensitive techniques have been developed to detect low concentrations of trace amines in the central nervous system. Such studies have revealed that trace amines in the central nervous system have a high turnover rate (Meek et al., 1970, *J. Neurochem.* 17: 1627-1635; Lemberger et al., 1971, *J. Pharmac. Exp. Ther.* 177:169-176; Wu & Boulton, 1974, *Can. J. Biochem.* 52:374-381; Durden & Philips, 1980, *J. Neurochem.* 34: 1725-1732). Trace amines are expressed throughout the brain in a heterogenous pattern and at least two of them can pass easily across the blood-brain-barrier (Boulton, 1974, *Lancet ii:* 7871; Oldendorf, 1971, *Am. Physiol.* 221: 1629-1639). Trace amines are also known to potentiate caudate neuronal firing in response to dopamine application and act as sympathomimetics by stimulating release of biogenic amines from brain preparations and synaptosomes when applied at high concentrations. Para-tyramine may act as a "false transmitter" in a manner similar to that of amphetamine by triggering release of neurotransmitters such as dopamine.

The abilities of p-tyramine and β-PEA to deplete neurotransmitter from storage vesicles, compete with neurotransmitters for uptake, and stimulate outward neurotransmitter flux through the plasma membrane carders are similar to the actions of the β-PEA analog, α-methyl-β-phenethylamine, better known as amphetamine (Amara and Sonders, 1998, *Drug Alcohol Depend* 51:87-96; Seiden et al., 1993). Amphetamines were originally marketed as stimulants and appetite suppressants, but their clinical use is now mostly limited to treating attention deficit hyperactivity disorder (Seiden et al., 1993, *Annu Rev Pharmacol Toxicol* 33:639-677): Although listed as controlled substances, amphetamines are widely consumed because of their ability to produce wakefulness and intense euphoria. Some substituted amphetamines, such as MDMAN ("ecstasy") and DOI, are taken for their "empathogenic" and hallucinogenic effects. (Eisner, 1994, *Ecstasy: The MDMA story.* Ronin Books, Berkeley, Calif.; Shulgin and Shulgin, 1991, *PiHKAL: A chemical love story.* Transform Press, Berkeley, Calif.). Numerous liabilities are associated with the use of amphetamines including hyperthermia (Byard et al., 1998, *Am J Forensic Med Pathol* 19:261-265), neurotoxicity (Ricaurte and McCann, 1992, *Ann NY Acad Sci* 648:371-382), psychosis (Seiden et al., 1993, ibid.), and psychological dependence (Murray, 1998, *J Psychol* 132: 227-237). In addition to the actions of amphetamines at biogenic amine transporters, it is also clear that a subset of amphetamine analogs, especially those with hallucinogenic properties, can act directly on 5-HT receptors as they have much higher affinities for these sites than for the transporters (Marek and Aghajanian, 1998, *Drug Alcohol Depend* 51:189-198).

The importance of biogenic amines and their receptors, particularly in the brain and central nervous system, has created the need for the isolation of additional biogenic amine receptors, particularly trace amine receptors, for the development of therapeutic agents for the treatment of disorders, including disorders of the CNS and most preferably treatment of disorders on mental health such as psychosis, in which biogenic amines and their receptors have been implicated. There is also a need for developing new tools that will permit identification of new drug lead compounds for developing novel drugs. This is of particular importance for psychoactive and psychotropic drugs, due to their physiological importance and their potential to greatly benefit human patients treated with such drugs. At present, few such economical systems exist. Conventional screening methods require the use of animal brain slices in binding assays as a first step. This is suboptimal for a number of reasons, including interference in the binding assay by non-specific binding of heterologous (i.e., non-receptor) cell surface proteins expressed by brain cells in such slices; differential binding by cells other than neuronal cells present in the brain slice, such as glial cells or blood cells; and the possibility that putative drug binding behavior in animal brain cells will differ from the binding behavior in human brain cells in subtle but critical ways. The ability to synthesize human biogenic amine receptor molecules in vitro would provide an efficient and economical means for rational drug design and rapid screening of potentially useful compounds. For these and other reasons, development of in vitro screening methods for psychotropic drugs has numerous advantages and is a major research goal in the pharmaceutical industry.

SUMMARY OF THE INVENTION

The present invention relates to the cloning, expression and functional characterization of a mammalian biogenic amine receptor gene. The invention comprises nucleic acids having a nucleotide sequence of a novel mammalian biogenic amine receptor gene that specifically binds to trace amines. The nucleic acids provided by the invention comprise a complementary DNA (cDNA) copy of the corresponding mRNA transcribed in vivo from the biogenic amine receptor genes of the invention. In one preferred embodiment, the mammalian biogenic amine receptor is a human biogenic amine receptor. In another preferred embodiments the mammalian biogenic amine receptor is a rat (Rattus norvegicus) biogenic amine receptor. Also provided are the deduced amino acid sequence of the cognate proteins of the cDNAs provided by the invention, methods of making said cognate proteins by expressing the cDNAs in cells transformed with recombinant expression constructs comprising said cDNAs, and said recombinant expression constructs and cells transformed thereby.

This invention in a first aspect provides nucleic acids, nucleic acid hybridization probes, recombinant eukaryotic expression constructs capable of expressing the biogenic amine receptors of the invention in cultures of transformed cells, and such cultures of transformed eukaryotic cells that synthesize the biogenic amine receptors of the invention. In another aspect, the invention provides homogeneous compositions of the biogenic amine receptor proteins of the invention, and membrane and cytosolic preparations from cells expressing the biogenic amine receptor proteins of the invention, as well as antibodies against and epitopes of the biogenic amine receptor proteins of the invention. The invention in another aspect provides methods for making said homogenous preparations and membrane and cytosolic preparations using cells transformed with the recombinant expression constructs of the invention and expressing said biogenic amine receptor proteins thereby. Methods for characterizing the receptor and biochemical properties of these receptor proteins and methods for using these proteins in the development of agents having pharmacological uses related to these receptors are also provided by the invention.

In a first aspect, the invention provides a nucleic acid having a nucleotide sequence encoding a mammalian biogenic amine receptor. In a first preferred embodiment, the nucleic acid encodes a human biogenic amine receptor. In this embodiment of the invention, the nucleotide sequence comprises 1125 nucleotides of human biogenic amine receptor cDNA comprising 1040 nucleotides of coding sequence, 20 nucleotides of 5' untranslated sequence and 85 nucleotides of 3' untranslated sequence is this embodiment of the invention, the nucleotide sequence of the biogenic amine receptor is the nucleotide sequence depicted in FIG. 1 (SEQ ID No:1). The sequence shown in FIG. 1 will be understood to represent one specific embodiment of a multiplicity of nucleotide sequences that encode the human biogenic amine receptor amino acid sequence (SEQ ID No.: 2) of the invention and that these different nucleotide sequences are functionally equivalent and are intended to be encompassed by the claimed invention. Further, it will be understood that the coding sequence comprising 1040 nucleotides can be used to express the cognate protein without inclusion of either the 5' or 3' untranslated sequences. In addition, it will be understood that different organisms and cells derived therefrom express preferentially certain tRNAs corresponding to subsets of the degenerate collection of tRNAs capable of encoding certain of the naturally-occurring amino acids, and that embodiments of the multiplicity of nucleotide sequences encoding the amino acid sequence of the human biogenic amine receptor protein of the invention that are optimized for expression in specific prokaryotic and eukaryotic cells are also encompassed by the claimed invention. Isolated nucleic acid derived from human genomic DNA and isolated by conventional methods using the human cDNA provided by the invention is also within the scope of the claimed invention. Finally, it will be understood that allelic variations of the human biogenic amine receptor, including naturally occurring and in vitro modifications thereof are within the scope of this invention. Each such variant will be understood to have essentially the same amino acid sequence as the sequence of the human biogenic amine receptor disclosed herein.

In a second preferred embodiment of this aspect of the invention, the nucleic acid encodes the rat biogenic amine receptor. In this embodiment of the invention, the nucleotide sequence includes 999 nucleotides of the rat biogenic amine receptor cDNA comprising the coding sequence. In this embodiment of the invention, the nucleotide sequence of the biogenic amine receptor is the nucleotide sequence depicted in FIG. 2 (SEQ ID No: 3). The sequence shown in FIG. 2 will be understood to represent one specific embodiment of a multiplicity of nucleotide sequences that encode the rat biogenic amine receptor amino acid sequence (SEQ ID No.:4) of the invention and that these different nucleotide sequences are functionally equivalent and are intended to be encompassed by the claimed invention. In addition, it will be understood that different organisms and cells derived therefrom express preferentially certain tRNAs corresponding to subsets of the degenerate collection of tRNAs capable of encoding certain of the naturally-occurring amino acids, and that embodiments of the multiplicity of nucleotide sequences encoding the amino acid sequence of the rat biogenic amine receptor protein of the invention that are optimized for expression in specific prokaryotic and eukaryotic cells are also encompassed by the claimed invention. Isolated nucleic acid derived from rat genomic DNA and isolated by conventional methods using the rat cDNA provided by the invention is also within the scope of the claimed invention. Finally, it will be understood that allelic variations of the rat biogenic amine receptor, including naturally occurring and in vitro modifications thereof are within the scope of this invention. Each such variant will be understood to have essentially the same amino acid sequence as the sequence of the human biogenic amine receptor disclosed herein.

Mammalian biogenic amine receptor proteins corresponding to the human and rat cDNAs of the invention are a second aspect of the claimed invention. In a first embodiment, the mammalian biogenic amine receptor protein is a human biogenic amine receptor having a deduced amino acid sequence shown in FIG. 1 (SEQ ID No.: 2). In a second embodiment is provided said human biogenic amine receptor protein comprising a membrane or cytosolic preparation from a cell, most preferably a recombinant cell, expressing a nucleic acid encoding a human biogenic amine of the invention. In a third embodiment, the mammalian biogenic amine receptor protein is a rat biogenic amine receptor having a deduced amino acid sequence shown in FIG. 2 (SEQ ID No.:4). In a fourth embodiment is provided said rat biogenic amine receptor protein comprising a membrane or cytosolic preparation from a cell, most preferably a recombinant cell, expressing a nucleic acid encoding a rat biogenic amine of the invention.

As provided in this aspect of the invention is a homogeneous composition of a mammalian biogenic amine receptor having a molecular weight of about 39 kD or derivative thereof that is a human biogenic amine receptor having an amino acid sequence shown in FIG. 1 and identified by SEQ ID No.: 2, said size being understood to be the predicted size of the protein before any post-translational modifications thereof. Also provided is a homogeneous composition of a mammalian biogenic amine receptor having a molecular weight of about 38 kD or derivative thereof that is a rat biogenic amine receptor having an amino acid sequence shown in FIG. 2 and identified by SEQ ID No.: 4, said size being understood to be the predicted size of the protein before any post-translational modifications thereof.

This invention provides both nucleotide and amino acid probes derived from the sequences herein provided. The invention includes probes isolated from either cDNA or genomic DNA, as well as probes made synthetically with the sequence information derived therefrom. The invention specifically includes but is not limited to oligonucleotide, nick-translated, random primed, or us vitro amplified probes made using cDNA or genomic clone of the invention encoding a mammalian biogenic amine receptor or fragment thereof and oligonucleotide and other synthetic probes synthesized chemically using the nucleotide sequence information of cDNA or genomic clone embodiments of the invention.

It is a further object of this invention to provide such nucleic acid hybridization probes to determine the pattern, amount and extent of expression of the biogenic amine receptor gene in various tissues of mammals, including humans. It is also an object of the present invention to provide nucleic acid hybridization probes derived from the sequences of mammalian biogenic amine receptor genes of the invention to be used for the detection and diagnosis of genetic diseases. It is an object of this invention to provide nucleic acid hybridization probes derived from the nucleic acid sequences of the mammalian biogenic amine receptor genes herein disclosed to be used for the detection of novel related receptor genes.

The present invention also includes synthetic peptides made using the nucleotide sequence information comprising the cDNA embodiments of the invention The invention includes either naturally occurring or synthetic peptides which may be used as antigens for the production of biogenic amine receptor-specific antibodies, or useful as competitors of biogenic amine receptor molecules for agonist, antagonist or drug binding, or to be used for the production of inhibitors of the binding of agonists or antagonists or analogues thereof to such biogenic amine receptor molecules.

The present invention also provides antibodies against and epitopes of the mammalian biogenic amine receptor molecules of the invention. It is an object of the present invention to provide antibodies that are immunologically reactive to the biogenic amine receptors of the invention. It is a particular object to provide monoclonal antibodies against these biogenic amine receptors. Hybridoma cell lines producing such antibodies are also objects of the invention. It is envisioned that such hybridoma cell lines may be produced as the result of fusion between a non-immunoglobulin producing mouse myeloma cell line and spleen cells derived from a mouse immunized with a cell line which expresses antigens or epitopes of a mammalian biogenic amine receptor of the invention. The present invention also provides hybridoma cell lines that produce such antibodies, and can be injected into a living mouse to provide an ascites fluid from the mouse that is comprised of such antibodies. It is a further object of the invention to provide immunologically-active epitopes of the mammalian biogenic amine receptor proteins of the invention. Chimeric antibodies immunologically reactive against the biogenic amine receptor proteins of the invention are also within the scope of this invention.

The present invention provides recombinant expression constructs comprising a nucleic acid encoding a mammalian biogenic amine receptor of the invention wherein the construct is capable of expressing the encoded biogenic amine receptor in cultures of cells transformed with the construct. A preferred embodiment of such constructs comprises a human biogenic amine receptor cDNA depicted in FIG. 1 (SEQ ID No.: 1), such constructs being capable of expressing the human biogenic amine receptor encoded therein in cells transformed with the construct. Another preferred embodiment of such constructs comprises a rat biogenic amine receptor cDNA depicted in FIG. 2 (SEQ ID No.: 3), such constructs being capable of expressing the rat biogenic amine receptor encoded therein in cells transformed with the construct.

The invention also provides prokaryotic and more preferably eukaryotic cells transformed with the recombinant expression constructs of the invention, each such cells being capable of and indeed expressing the mammalian biogenic amine receptor encoded in the transforming construct, as well as methods for preparing mammalian biogenic amine receptor proteins using said transformed cells.

The present invention also includes within its scope protein preparations of prokaryotic and eukaryotic cell membranes containing the biogenic amine receptor protein of the invention, derived from cultures of prokaryotic or eukaryotic cells, respectively, transformed with the recombinant expression constructs of the invention. The present invention also includes within its scope protein preparations of prokaryotic and eukaryotic cytoplasmic fractions containing the biogenic amine receptor protein of the invention, derived from cultures of prokaryotic or eukaryotic cells, respectively, transformed with the recombinant expression consists of the invention.

The invention also provides methods for screening compounds for their ability to inhibit, facilitate or modulate the biochemical activity of the mammalian biogenic amine receptor molecules of the invention, for use in the in vitro screening of novel agonist and antagonist compounds. In preferred embodiments, cells transformed with a recombinant expression construct of the invention are contacted with such a compound, and the binding capacity of the compounds, as well as the effect of the compound on binding of other, known biogenic amine receptor agonists and antagonists, is assayed. Additional preferred embodiments comprise quantitative analyses of such effects.

The present invention is also useful for the detection of analogues, agonists or antagonists, known or unknown, of the mammalian biogenic amine receptors of the invention, either naturally occurring or embodied as a drug. In preferred embodiments, such analogues, agonists or antagonists may be detected in blood, saliva, semen, cerebrospinal fluid, plasma, lymph, or any other bodily fluid.

The biogenic amine receptors of the present invention are directly activated by a wide variety of clinically and socially import drugs, including amphetamines, ergot derivatives, and adrenergic agents. Thus, the receptors of the invention are useful for developing alternative pharmaceutical agents having the beneficial properties of these drugs without at least some of the deleterious effects, for example a propensity for addiction, as well as compounds that can inhibit or overcome said propensity for addition.

Specific preferred embodiments of the present invention will become evident from the following more detailed description of certain preferred embodiments and the claims.

DESCRIPTION OF THE DRAWINGS

FIG. 1 illustrates the nucleotide (SEQ ID No.: 1) and amino acid (SEQ ID No.:2) sequences of a human trace amine receptor.

FIG. 2 illustrates the nucleotide (SEQ ID No.: 3) and amino acid (SEQ ID No.:4) sequences of a rat trace amine receptor.

FIG. 3 presents deduced amino acid sequences for the rat and human trace receptors aligned with other homologous G protein-coupled receptors. Identities are outlined in black. Abbreviations are: rTAR, rat trace amine receptor, hTAR, human trace amine receptor, NTIR, orphan NeuroTransmitter receptor, orphan GPCR57 and 58; D1R, dopamine D1 receptor, B2aR, B2 adrenergic receptor, 5HT4c, serotonin 5HT4C receptor. Arrowheads indicate positions designated as 5.42 and 5.43.

FIG. 5A is a photograph of an ethidium bromide-stained and ultraviolet light irradiated agarose gel containing DNA fragments produced by RT-PCR of RNA from rat brain tissues. The PCR products resolved on this gel are from the following rat brain regions, from which cDNA was synthesized from oligo(dT)-primed total RNA: lane 1, pituitary gland; lane 2, hindbrain; lane 3, midbrain; lane 4, locus coeruleus; lane 5, hypothalamus; lane 6, striatum; lane 7, olfactory bulb; lane 8, olfactory tubercle; lane 9, hippocampus; lane 10, cortex; lane 11, cerebellum; lane 12, thalamus; lane 13, 1:100 dilution of human trace amine plasmid DNA.

FIG. 6 is a photograph of an autoradiogram of Northern analysis of RNA from various rat cell lines expressing the rat trace amine receptor of the invention after transfection with a recombinant expression construct encoding the rat receptor. RNA shown in this gel was obtained from the following cell lines: lane 1, LBP; lane 2, baby hamster kidney (BHK) cells; lane. 3, rat insulinoma (RIN5) cells; lane 4, AR42J rat pancreatic-tumor cell line; lane 5, CHW cells; lane 6, GH4 rat pituitary cells; lane 7, GH3 rat pituitary cells; lane 8, AtT20 rat pituitary cells; lane 9, PC12 rat adrenal gland cells; lane 10, SK-N-MC human neuroblastoma cells; lane 11, N4TG1 rat neuroblastoma cells; lane 12, NB4 cells; lane 13, LCS cells; lane 14, R2C rat Ledig cells.

FIG. 8B is an autoradiogram of a nylon membrane containing DNA fragments transferred from the agarose gel shown in FIG. 8A and probed with $^{32}$P-labeled nucleic acid prepared from the full-length rat genomic clone encoding the rat trace amine receptor of the invention.

DETAILED DESCRIPTION OF THE PREFERRED EMBODIMENTS

Figure 4:
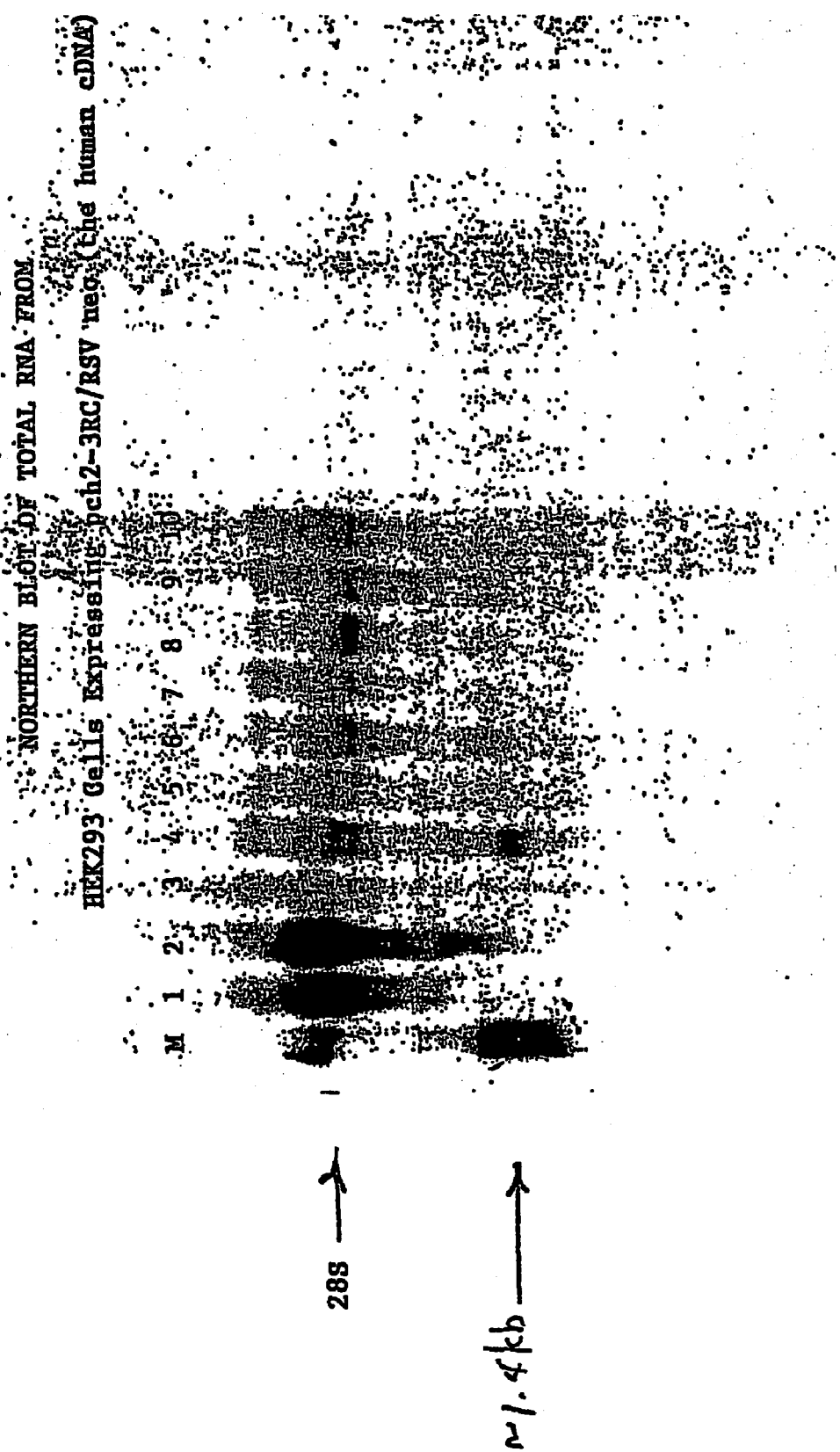
FIG. 4 is a photograph of an autoradiogram of Northern analysis of total cellular RNA (20 µg/lane) from human HEK293 cells expressing the human biogenic amine receptor of the invention after transformation with a recombinant expression construct.

The terms "mammalian biogenic amine receptor" and "trace amine receptor" as used herein refer to proteins consisting essentially of and having substantially the same biological activity as, the protein encoded by the amino acid depicted in FIG. 1 (SEQ ID No.: 2) and FIG. 2 (SEQ ID No.: 4). This definition is intended to encompass natural allelic variations in the disclosed biogenic, trace amine receptor. Cloned nucleic acid provided by the present invention may encode trace amine receptor protein of any species of origin, including, for example, mouse, rat, rabbit, cat, and human, but preferably the nucleic acid provided by the invention encodes trace amine receptors of mammalian, most preferably rat and human, origin.

The nucleic acids provided by the invention comprise DNA or RNA having a nucleotide sequence encoding a mammalian trace amine receptor. Specific embodiments of said nucleic acids are depicted in FIG. 1 (SEQ ID No.: 1) or FIG. 2 (SEQ ID No.: 3), and include any nucleotide sequence encoding a mammalian biogenic amine receptor having an amino acid sequence as depicted in FIG. 1 (SEQ ID No.: 2) or FIG. 2 (SEQ ID No.: 4). Nucleic hybridization probes as provided by the invention comprise any portion of a nucleic acid of the invention effective in nucleic acid hybridization under stringency conditions sufficient for specific hybridization. Mixtures of such nucleic acid hybridization probes are also within the scope of this embodiment of the invention. Nucleic acid probes as provided herein are useful for isolating mammalian species analogues of the specific embodiments of the nucleic acids provided by the invention. Nucleic acid probes as provided herein are also useful for detecting mammalian trace amine receptor gene expression in cells and tissues using techniques well-known in the art, including but not limited to Northern blot hybridization, in situ hybridization and Southern hybridization to reverse transcriptase—polymerase chain reaction product DNAs. The probes provided by the present invention, including oligonucleotides probes derived therefrom, are also useful for Southern hybridization of mammalian preferably human, genomic DNA for screening for restriction fragment length polymorphism HEILP) associated with certain genetic disorders.

The production of proteins such as mammalian biogenic amine receptors from cloned genes by genetic engineering means is well known in this art. The discussion that follows is accordingly intended as an overview of this field, and is not intended to reflect the full state of the art.

Nucleic acid encoding a trace amine receptor may be obtained, in view of the instant disclosure, by chemical synthesis, by screening reverse transcripts of mRNA from appropriate cells or cell line cultures, by screening genomic libraries from appropriate cells, or by combinations of these procedures, in accordance with known procedures as illustrated below. Additionally, sequences of such receptors can be obtained from any species in which the content of the species genomic DNA has been determined and assembled in a database or other searchable compilation, using search programs known in the art and the sequences of the trace amine receptors disclosed herein. Screening of mRNA or genomic DNA may be carried out with oligonucleotide probes generated from the nucleic acid sequence information from mammalian trace amine receptor nucleic acid as disclosed herein. Probes may be labeled with a detectable group such as a fluorescent group, a radioactive atom or a chemiluminescent group in accordance with known procedures and used in conventional hybridization assays, as described in greater detail in the Examples below. In the alternative, mammalian biogenic amine receptor nucleic acid sequences may be obtained by use of the polymerase chain reaction (PCR) procedure, using PCR oligonucleotide primers corresponding to nucleic acid sequence information derived from a biogenic amine receptor as provided herein. See U.S. Pat. Nos. 4,683,195 to Mullis et al. and 4,683,202 to Mullis.

Mammalian trace amine receptor protein may be synthesized in host cells transformed with a recombinant expression construct comprising a nucleic acid encoding said receptor and comprising genomic DNA or cDNA. Such recombinant expression constructs can also be comprised of a vector that is a replicable DNA construct Vectors are used herein either to amplify DNA encoding a trace amine receptor and/or to express DNA encoding a trace amine receptor gene. For the purposes of this invention, a recombinant expression construct is a replicable DNA, construct in which a nucleic acid encoding a trace amine receptor is operably linked to suitable control sequences capable of effecting the expression of the receptor in a suitable host.

The need for such control sequences will vary depending upon the host selected and the transformation method chosen. Generally, control sequences include a transcriptional promoter, an optional operator or enhancer sequence to control transcription, a sequence encoding suitable mRNA ribosomal binding sites, and sequences that control the termination of transcription and translation. Amplification vectors do not require expression control domains. All that is needed is the ability to replicate in a host, usually conferred by an origin of replication, and a selection gene to facilitate recognition of transformants. See, Sambrook et al., 1990, *Molecular Cloning: A Laboratory Manual* (Cold Spring Harbor Press: New York).

Vectors useful for practicing the present invention include plasmids, viruses (including phage and mammalian DNA and RNA viruses), retroviuses, and integratable DNA fragments (i.e, fragments integratable into the host genome by homologous recombination). The vector can replicate the gene of interest and function independently of the host genome, or can, in some instances, integrate into the genome itself. Suitable vectors will contain replicon and control sequences which are derived from species compatible with the intended expression host A preferred vector is RcRSV (obtained from bivitrogen, San Diego, Calif.). Another preferred vector is pcDNA3.1/V5/His-TOPO (Invitrogen, San Diego, Calif.). The pcDNA3.1/V5/His-TOPO vector expresses a receptor preceded at its amino terminus by a cleavable 16 amino acid signal sequence of the influenza hemaglutinin virus immediately followed by the 8 amino acid M1-Flag epitope and then a two amino acid linker (MetGly) just before the initiation methionine (Guan et al., 1992, *J Biol Chem*, 267:21995-21998).

Transformed host cells are cells that have been transformed or transfected with recombinant expression constructs made using recombinant DNA techniques and comprising nucleic acid encoding a trace amine receptor protein. Cultures of cells derived from multicellular organisms are a desirable host for recombinant biogenic amine receptor protein synthesis. In principal, any higher eukaryotic cell culture is useful, whether from vertebrate or invertebrate culture. However, mammalian cells are preferred, as illustrated in the Examples. Propagation of such cells in cell culture has become a routine procedure. See *Tissue Culture*, Academic Press, Kruse & Patterson, editors (1973). Exmples of useful host cell lines are human embryonic kidney (HEK) 293 cells, VERO and HeLa cells, Chinese hamster ovary (CHO) cell lines, mouse Ltk$^-$ cell lines and WI138, BEK, COS-7, CV, and MDCK cell lines. Preferred host cells are HEK293 cells, COS-7 cells (Gluzman, 1981, Cell 23: 175-182) and Ltk$^-$ cells. Transformed host cells may express the trace amine receptor protein, but host cells transformed for purposes of cloning or amplifying nucleic acid hybridization probe DNA need not express the receptor. The trace amine receptor of the invention can be located in the host cell cytosol. Accordingly, the invention provides preparations of cell cytosolic fractions comprising the trace amine receptor protein of the invention, as well as purified, homogeneous preparations of the receptor protein itself. See, Sambrook et al., ibid. The receptor of the invention may also be located in membranes from the host cell. Therefore, the invention provides preparations of said cell membranes comprising the trace amine receptor protein of the invention. See, Sambrook et al., ibid.

The invention provides homogeneous compositions of mammalian trace amine receptor protein produced by transformed eukaryotic cells as provided herein. Each such homogeneous composition is intended to be comprised of a trace amine receptor protein that comprises at least 75%, more preferably at least 80%, and most preferably at least 90% of the protein in such a homogenous composition; in said homogeneous preparations, individual contaminating protein species are expected to comprise less than 5%, more preferably less than 2% and most preferably less than 1% of the preparation. The invention also provides membrane and cytosolic preparations from cells expressing mammalian trace amine receptor protein as the result of transformation with a recombinant expression construct, as described herein. Mammalian trace amine receptor proteins made from cloned genes in accordance with the present invention may be used for screening trace amine analogues, or trace amine receptor agonists or antagonists of trace amine binding, or for determining the amount of such agonists or antagonists are present in a solution of interest (e.g., blood plasma, cerebrospinal a fluid or serum). For example, host cells may be transformed with a recombinant expression construct of the present invention, a mammalian trace amine receptor expressed in those host cells, and the cells, membranes or cytosolic fractions thereof used to screen compounds for their effect on trace amine receptor agonist binding activity. By selection of host cells that do not ordinarily express a trace amine receptor, pure preparations of membranes or cytosolic fractions containing the receptor can be obtained. In a preferred embodiment, agonists (also referred to herein as stimulators) of the receptor of the present invention can be endogenous neurotransmitters or drugs. Neurotransmitters and drugs that activate the receptor are further described n the Examples section herein, and include p-tyramine, phenylethylamine, tryptamine, octopamine, synephrine, dopamine, serotonin, m-tyramine, amphetamines, methamphetamines, MDMA, p-chloroamphetraine, betahistine, 1-phenylpiporazine phenylephrine, apomorphine, metergoline, and ergot alkaloids. Agonists, for the trace amine receptor include, but are not limited to phenethylamine (PEA), hordenine, L-tyrosinol, S,R-amphetamine (+and −), 4-OH—R(−)-amphetamine, mnethamphetamine (+and −), (±)DOI, phenelzine, tranylcypromine, 3,4DiMeo-PEA>Mescaline, (±)MDMA, 3,4 dihydroxybenzylguanidine, 3-phenylpropylamine, N,N-dimethylpropiophenone, N-phenylethylenediamine kynuramine, 4-phenylbutylamine, tryptamine, 2-thiopheneethylamine, betahistne, 2>4>3-pyridylethylamine, 1-phenylpiperazine, 1-(1-napthyl)piperazine, 1,2,3,4-tetrahydroisoquinoline, (±)salsolinol, hydrocotamine, nomifensine, R(−)apomorphine, S(+)2-aminotetralin, R(−)2-aminotetralin, (±)2-amino-1,2-dihydronapthalene, (±)3A6HC, (±)2-aminoindan, MRTP, 4-phenyl-1,2,3,6-tetrahydropyridine, tolazoline, naphazoline, phentolamine, agroclavine, bromocriptine, lisuride, d-LSD, metergoline, (±)fenfluramine, fenspiride, 2-phenyl-2-imidazoline, methylphenidate, pargyline, 2,2-diphenylethylamine, trans-cinnamyl-piperazine, 1-benzyl-piperidine, rimantidine, tripelennamine, tryptamine/5-MeO-DMT, forskolin, amphetamine/phentermine, cyproheptadine, dopamine, dihydroergotamine, fenoterol, HVA:D1 receptor, imidazoline/naphazoline, imidazoline/oxymetazoline, imidazoline/phentolamine, imidazoline/tolazoline, isoproterenol, metanephrine DL, methamphetamine/2-MeO, octopamine, PEA/2-amino 4-OH, PEA/3,4 dinethoxy, 4-OH-PEA/3-MeO, 4-amino-PEA, 4-methoxy-PEA, AEBSF-PEA, phenylephrine, piperazine/mCPP, piperazine/TFMPP, phenylpiperazine, prenylamine, 2-(2aminoethyl)pyradine, 3-(2aminoethyl)pyradine, 4-(2aminoethyl)pyradine, ritodrine, synephrine, tetralin/ADTN/6,7, 5-Fluoro-tryptamine, N,N-dimethyl-tryptamine, tryptophanol (±), m-tyramine, p-tyramine, and most preferably 3-hyrdoxytyramine. Antagonists of the trace amine receptor include, but are not limited to phenylalanine, (±)N-ethylamphetamine, propylhexedrine, fenfluramine, deprenyl norepinephrine, epinephrine, N,N,N-trimethyldopamine, dopamine-guanidine, dimethylsulfonium-DA, benzylamine, pargyline, tryptophan, 5-carbooxamidotyptamine, histamine, 2-(2aminoethyl)1,3-dioxolane, iproniazid, isoniazid, 1,1-dimethyl-4-phenylpiperazinium, trans-1-cinnamylpiperazine, 1-(4Acetophenone)piperazine, quipazine, SH-1-101, PAPP (LY165,163), 4-OH, 4-phenylpiperidine, HA-1, HA-2, HA-3, HA-4, HA-5, prazosin, 4-phenylpyrimidine, hydrastinine, boldine, (+)butaclamol 3-aminocoumarin, MPP+, clonidine, methysergide, aminorex, norapomorphine, N-butyl-amphetamine, benztropine, cis-fluphenthixol, diphenylpyraline flunarizine, fluspirilene, GBR 12909, GBR 12935, LY (741, 626), nicardipine, reserpine, ritanserin, spiperone, thioridazine, and trifluoperazine.

A compound identified in a screen may be useful for treating various conditions associated with effects of unregulated trace amine activity as a result of endogenous or exogenous stimulation. The present invention provides a pharmaceutical composition comprising the compound in admixture with a pharmaceutically acceptable carrier. In a preferred embodiment, a therapeutically effective amount of the pharmaceutical composition is administered to a patient with a condition associated with unregulated trace amine activity. For example, the pharmaceutical composition of the present invention can be used to reduce sympathomimetic effects of enhanced trace amine transmission induced by elevated levels of trace amines or certain drugs. Common sympathomimetic effects include rapid heart rate, high blood pressure, agitation, cardiac arrythmia, seizures, and coma.

The pharmaceutical composition can also be used to treat peripheral effects of drugs, such as amphetamine. For example, the pharmaceutical composition of the present invention can be used to treat hyperthermia caused by amphetamine action. Some conditions that can be treated using a pharmaceutical composition of the present invention are pathological, such as schizophrenia, depression, etc. In addition, the pharmaceutical composition of the present invention can be used to treat drug addiction in a mammal, preferably a human.

Pharmaceutical compositions of the present invention can be manufactured in a manner that is itself known, e.g., by means of a conventional mixing, dissolving, granulating, dragee-making, levigating, emulsifying, encapsulating, entrapping or lyophilizing processes.

Pharmaceutical compositions of the compounds of the present invention can be formulated and administered through a variety of means, including systemic, localized, or topical administration. Techniques for formulation and administration can be found in "Remington's Pharmaceutical Sciences," Mack Publishing Co., Easton, Pa. Pharmaceutical compositions for use in accordance with the present invention thus can be formulated in conventional manner using one or more physiologically acceptable carriers comprising excipients and auxiliaries that facilitate processing of the active compounds into preparations that can be used pharmaceutically. Proper formulation is dependent upon the route of administration chosen.

Non-toxic pharmaceutical salts include salts of acids such as hydrochloric, phosphoric, hydrobromic, sulfuric, sulfuric, formic, toluenesulfonic, methanesulfonic, nitic, benzoic, citric, tararic, maleic, hydroiodic, alkanoic such as acetic, HOOC—$(CH_2)_n$—$CH_3$ where n is 0-4, and the like. Non-toxic pharmaceutical base addition salts include salts of bases such as sodium, potassium, calcium, ammonium, and the like. Those skilled in the art will recognize a wide variety of non-toxic pharmaceutically acceptable addition salts.

For injection, the compounds of the invention can be formulated in appropriate aqueous solutions, such as physiologically compatible buffers such as Hanks's solution, Ringer's solution, or physiological saline buffer. For transmucosal and transcutaneous administration, penetrants appropriate to the barrier to be permeated are used in the formulation. Such penetrants are generally known in the art.

For oral administration, the compounds can be formulated readily by combining the active compounds with pharmaceutically acceptable carriers well known in the arts. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, to potato starch, gelatin, gum tragacanth, methyl cellulose, hydroxypropylmethylcellulose, sodium carboxymethylcellulose, and/or polyvinylpyrrolidone (PVP). If desired, disintegrating agents can be added, such as the cross-linked polyvinyl pyrrolidone, agar, or alginic acid or a salt thereof such as sodium alginate.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active compounds in admixture with filer such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration. For buccal administration, the compositions can take the form of tablets or lozenges formulated in conventional manner.

For administration by inhalation, the active compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler or insufflator can be formulated containing a powder mix of the active compound and a suitable powder base such as lactose or starch.

The active compounds can be formulated for parenteral administration by injection, e.g. by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances that increase the viscosity of the suspension, such as sodium carboxymethyl cellulose, sorbitol, or dextran. Optionally, the suspension can also contain suitable stabilizers or agents that increase the solubility of the compounds to allow for the preparation of highly concentrated solutions. Alternatively, the active compounds can be in powder form for constitution with a suitable vehicle, e.g., sterile pyrogen-free water, before use. The active compounds can also be formulated in rectal compositions such as suppositories or retention enemas, e.g., containing conventional suppository bases such as cocoa butter or other glycerides.

In addition to the formulations described previously, the active compounds can also be formulated as a depot preparation. Such long acting formulations can be administered by implantation (for example subcutaneously or intramuscularly) or by intramuscular injection. Thus, for example, the active compounds can be formulated with suitable, polymeric or hydrophobic materials (for example as an emulsion in an acceptable oil) or ion exchange resins, or as sparingly soluble derivatives, for example, as a sparingly soluble salt.

The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

The active compounds of the invention can be provided as salts with pharmaceutically compatible counterions. Pharmaceutically compatible salt can be formed with many acids, including but not limited to hydrochloric, sulfuric, acetic, lactic, tartaric, malic, succinic, phosphoric, hydrobromic, sulfinic, formic, toluenesulfonic, methanesulfonic, nitic, benzoic, citric, tartaric, maleic, hydroiodic, alkanoic such as acetic, HOOC—$(CH_2)_n$—$CH_3$ where n is 0-4, and the like. Salts tend to be more soluble in aqueous or other protonic solvents that are the corresponding free base forms. Non-toxic pharmaceutical base addition salts include salts of bases such as sodium, potassium calcium, ammonium, and the like. Those skilled in the art will recognize a wide variety of non-toxic pharmaceutically acceptable addition salts.

The mode of administration can be selected to maximize delivery to a desired target site in the body. Suitable routes of administration can, for example, include oral, rectal, transmucosal, transcutaneous, or intestinal administration; parenteral delivery, including intramuscular, subcutaneous, intramuscular injections, as well as intrathecal direct intraventricular, intravenous, intraperitoneal intranasal, or rather than systemic manner, for example, via injection of the compound directly into a specific tissue, often in a depot or sustained release formulation.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing, symptoms of the subject being treated. Determination of the effective amounts is well within the capability of those skilled in the art especially in light of the detailed disclosure provided herein.

For any compound used in the method of the invention, the therapeutically effective dose can be estimated initially from cell culture assays, as disclosed herein. For example, a dose can be formulated in animal models to achieve a circulating concentration range that includes the EC50 (effective dose for 50% increase) as determined in cell culture, i.e., the concentration of the test compound which achieves a half-maximal inhibition of tumor cell growth in vitro. Such information can be used to more accurately determine useful doses in humans.

It will be understood, however, that the specific dose level for any particular patient will depend upon a variety of factors including the activity of the specific compound employed, the age, body weight, general health sex, diet, time of administration, route of administration, and rate of excretion, drug combination, the severity of the particular disease undergoing therapy and the judgment of the prescribing physician.

For administration to non-human animals, the drug or a pharmaceutical composition containing the drug may also be added to the animal feed or drinking water. It will be convenient to formulate animal feed and drinking water products with a predetermined dose of the drug so that the animal takes in an appropriate quantity of the drug along with its diet. It will also be convenient to add a premix containing the drug to the feed or drinking water approximately immediately prior to consumption by the animal.

Toxicity and therapeutic efficacy of such compounds can be determined by standard pharmaceutical procedures in cell cultures or experimental animals, e.g., for determining the LD50, (the dose lethal to 50% of the population) and the ED50 (the dose therapeutically effective in 50% of the population). The dose ratio between toxic and therapeutic effects is the therapeutic index and it can be expressed as the ratio between LD50 and ED50. Compounds that exhibit high therapeutic indices are preferred. The data obtained from these cell culture assays and animal studies can be used in formulating a range of dosage for use in humans. The dosage of such compounds lies preferably within a range of circulating concentrations that include the ED50 with little or no toxicity. The dosage can vary within this range depending upon the dosage form employed and the route of administration utilized. The exact formulation, route of administration and dosage can be chosen by the individual physician in view of the patient's condition. (See, e.g. Fingl et al., 1975, in "The Pharmacological Basis of Therapeutics", Ch.1, p.1).

The recombinant expression constructs of the present invention are useful in molecular biology to transform cells that do not ordinarily express a trace amine receptor to thereafter express this receptor. Such cells are useful as intermediates for making cell membrane or cytosolic preparations useful for receptor binding activity assays, which are in turn useful for drug screening. The recombinant expression constructs of the present invention thus provide a method for screening potentially useful drugs at advantageously lower cost than conventional animal screening protocols. While not completely eliminating the need for ultimate in vivo activity and toxicology assays, the constructs and cultures of the invention provide an important first screening step for the vast number of potentially useful drugs synthesized, discovered or extracted from natural sources each year.

The recombinant expression constructs of the present invention are useful in molecular biology to detect, isolate, characterize and identify novel endogenous trace amine receptor agonists and antagonists found in plasma, serum, lymph, cerebrospinal fluid, seminal fluid, or other potential sources of such compounds. This utility thereby enables rational drug design of novel therapeutically-active drugs using currently-available techniques (see Walters, "Computer-Assisted Modeling of Drugs", in Klegerman & Groves, eds., 1993, *Pharmaceutical Biotechnology*, Interpharm Press: Buffalo Grove, Ill., pp. 165-174).

The recombinant expression constructs of the present invention may also be useful in gene therapy. Cloned genes of the present invention, or fragments thereof, may also be used in gene therapy carried out homologous recombination or site-directed mutagenesis. See generally Thomas & Capecchi, 1987, *Cell* 51: 503-512; Bertling, 1987, Bioscience Reports. 7: 107-112; Smithies et al., 1985, Nature 317: 230-234.

Nucleic acid and oligonucleotide probes as provided by the present invention are useful as diagnostic tools for probing trice amine receptor gene expression in tissues of humans and other annals. For example, tissues are probed in situ with oligonucleotide probes carrying detectable groups by conventional autoradiographic or other detection techniques, to investigate native expression of this receptor or pathological conditions relating thereto. Further, chromosomes can be probed to investigate the presence or absence of the corresponding trace amine receptor gene, and potential pathological conditions related thereto.

The invention also provides antibodies that are immunologically reactive to the trace amine receptor protein or epitopes thereof provided by the invention. The antibodies provided by the invention may be raised, using methods well known in the art, in animals by inoculation with cells that express a trace amine receptor or epitopes thereof cell membranes from such cells, whether crude membrane preparations or membranes purified using methods well known in the art, cytosolic preparations, or purified preparations of proteins, including fusion proteins, particularly fusion proteins comprising epitopes of the trace amine receptor protein of the invention fused to heterologous proteins and expressed using genetic engineering means in bacterial, yeast or eukaryotic cells, said proteins being isolated from such cells to varying degrees of homogeneity using conventional biochemical methods. Synthetic peptides made using established synthetic methods in vitro and optionally conjugated with heterologous sequences of amino acids, are also encompassed in these methods to produce the antibodies of the invention. Animals that are useful for such inoculations include individuals from species comprising cows, sheep, pigs, chickens, mice, rats, rabbits, hamsters, goats and primates. Preferred animals for inoculation are rodents (including mice, rats, hamsters) and rabbits. The most preferred animal is the mouse.

Cells that can be used for such inoculations, or for any of the other means used in the invention, include any cell line which naturally expresses the trace amine receptor provided by the invention, or more preferably any cell or cell line that expresses the trace amine receptor of the invention, or any epitope thereof, as a result of molecular or genetic engineering, or that has been treated to increase the expression of an endogenous or heterologous trace amine receptor protein by physical, biochemical or genetic means. Preferred cells are mammalian cells, most preferably cells syngeneic with a rodent, most preferably a mouse host, that have been transformed with a recombinant expression construct of the invention encoding a trace amine receptor protein, and that express the receptor therefrom.

The present invention also provides monoclonal antibodies that are immunologically reactive with an epitope derived from a trace amine receptor of the invention, or fragment thereof, present on the surface of such cells. Such antibodies are made using methods and techniques well known to those of skill in the art. Monoclonal antibodies provided by the present invention are produced by hybridoma cell lines, that are also provided by the invention and that are made by methods well known in the art.

Hybridoma cell lines are made by fusing individual cells of a myeloma cell line with spleen cells derived from animals immunized with cells expressing a trace amine receptor of the invention, as described above. The myeloma cell lines used in the invention include lines derived from myelomas of mice, rats, hamsters, primates and humans. Preferred myeloma cell lines are from mouse, and the most preferred mouse myeloma cell line is P3X63-Ag8.653. The animals from which spleens are obtained after immunization are rats, mice and hamsters, preferably mice, most preferably Balb/c mice. Spleen cells and myeloma cells are fused using a number of methods well known in the art, including but not limited to incubation with inactivated Sendai virus and incubation in the presence of polyethylene glycol CPEG). The most preferred method for cell fusion is incubation in the presence of a solution of 45% (w/v) PEG-1450. Monoclonal antibodies produced by hybridoma cell lines can be harvested from cell culture supernatant fluids from in vitro cell growth; alternatively, hybridoma cells can be injected subcutaneously and/or into the peritoneal cavity of an animal most preferably a mouse, and the monoclonal antibodies obtained from blood and/or ascites fluid.

Monoclonal antibodies provided by the present invention are also produced by recombinant genetic methods well known to those of skill in the art, and the present invention encompasses antibodies made by such methods that are immunologically reactive with an epitope of a trace amine receptor of the invention. The present invention also encompasses fragments including but not limited to F(ab) and F(ab)$'_2$ fragments, of such antibody. Fragments are produced by any number of methods, including but not limited to proteolytic or chemical cleavage, chemical synthesis or preparation of such fragments by means of genetic engineering technology. The present invention also encompasses single-chain antibodies that are immunologically reactive with an epitope of a trace amine receptor, made by methods known to those of skill in the art.

The present invention also encompasses an epitope of a trace amine receptor of the invention, comprised of sequences and/or a conformation of sequences present in the receptor molecule. This epitope may be naturally occurring, or may be the result of chemical or proteolytic cleavage of a receptor molecule and isolation of an epitope containing peptide or may be obtained by chemical or in vitro synthesis of an epitope-containing peptide using methods well known to those skilled in the art. The present invention also encompasses epitope peptides produced as a result of genetic engineering technology and synthesized by genetically engineered prokaryotic or eukaryotic cells.

The invention also includes chimeric antibodies comprised of light chain and heavy chain peptides immunologically reactive to a biogenic amine receptor-derived epitope. The chimeric antibodies embodied in the present invention include those that are derived from naturally occurring antibodies as well as chimeric antibodies made by means of genetic engineering technology well known to those of skill in the art.

The Examples that follow are illustrative of specific embodiments of the invention, and various uses thereof. They set forth for explanatory purposes only, and are not to be taken as limiting the invention.

EXAMPLE 1

Isolation of a Mammalian Biogenic Amine Receptor Probe by Random PCR Amplification of Rat Insulinoma cDNA Using Degenerate Oligonucleotide Primers In order to clone novel mammalian G-protein coupled receptors, cDNA prepared from total cellular RNA obtained from a rat pancreatic tumor cell line AR42J (ATCC Accession No. CRL-1492) was used as template for a polymerase chain reaction (PCR)-based random cloning experiment PCR was performed using a pair of degenerate oligonucleotide primers corresponding to a consensus sequence of the third and sixth transmembrane regions of known G-coupled receptors. PCR products obtained in this experiment were characterized by nucleotide sequencing. A full length clone was obtained by screening a rat genomic library using a cloned PCR product encoding a novel G-protein coupled receptor as deduced by nucleotide sequencing and comparison with a sequence database (GenBank).

The PCR amplification experiments were performed as follows. Total RNA was isolated from AR42J cells by the guanidinium thiocyanate method (Chirgwin et al., 1979, Biochemistry 18: 5294-5299). First-strand cDNA was prepared from this RNA using standard techniques (see Sambrook et al, 1990, *Molecular Cloning: A Laboratory Manual*, Cold Spring Harbor Press, Cold Spring Harbor Laboratory, N.Y.) using murine reverse transcriptase (BRL, Gaithersburg, Md.) and oligo-dT priming (Sambrook et al., ibid.). The rat cDNA preparation was then subjected to 35 cycles of PCR amplification using 500 picomoles of degenerate oligonucleotide primers having the following sequence:

```
Primer III (sense):
                                    (SEQ ID NO: 5)
GAGTCGACCTGTG(C/T)G(C/T)(C/G)AT(C/T)(A/G)CIIT(G/T)

GAC(C/A)G(C/G)TAC and

Primer VI (antisense):
                                    (SEQ ID NO: 6)
CAGAATTCAG(T/A)AGGGCAICCAGCAGAI(G/C)(G/A)(T/C)GAA
``` in 30 μL of a solution containing 50 mM Tris-HCl (pH 8.3), 2.5 mM MgCl2, 0.01% gelatin, 250 μM each dNTP, and 2.5 units of Taq polymerase (Saiki et al., 1988, Science 239: 487-491). Each PCR amplification cycle consisted of incubations at 94° C. for. 90 sec (denaturation), 50° C. for 90 see (annealing), and 72° C. for 120 sec (extension) for 35 cycles.

Amplified products of the PCR reaction were separated on a 1.0% agarose gel (see Sambrook et al., ibid.), and fragments ranging in size from 400 basepairs (bps) to 750 bp were subcloned in the plasmid vector pBluescript (Stratagene, LaJolla, Calif.). Plasmid DNA from these clones was purified and the nucleotide sequence of the insert ODNA determined by the dideoxynucleotide chain Lamination method (Sanger et al, 1977, Proc. Natl. Acad. Sci USA 74: 5463-5467) using Sequenase® (U.S. Biochemical Corp., Cleveland, Oreg.). PCR products were identified by screening the GenBank database and identified a cloned fragment having a high degree of homology to known biogenic amine receptors, as well as containing sequence motifs that are common to the G-protein coupled family of receptors, but that was not identical to any previously-identified biogenic amine receptor sequence.

EXAMPLE 2

Isolation of a Novel Mammalian Trace Amine Receptor cDNA

The cloned PCR product obtained in Example 1 was used to isolate a full-length clone from a rat genomic DNA library (obtained from Clonetech, Palo Alto, Calif.) as follows.

The 0.4 kb DNA fragment generated by PCR having high homology to known biogenic amine receptors was $^{32}$P-labeled using the random priming technique (Stratagene, San Diego Calif.). This probe was used to screen a rat genomic library that had been transferred to nylon membranes (Gene Screen Plus, NEN, Boston Mass.). Hybridization was performed in 50% formamide, 5×SSC, 1% SDS, 5× Denhardt' solution, and salmon sperm DNA (50 µg/mL) with the radioactive probe at 2×10$^6$ cpm/mL at 37° C. for overnight. The nylon filters were then washed as follows: at room temperature in a solution of 2×SSC/0.1% SDS for 10 minutes, followed by a wash at 55° C. in a solution of 2×SSC/0.1% SDS for 15 minutes, and finally awash at 55° C. in a solution of 0.5×SSC/0.1% SDS for 5 minutes. Filters were then exposed to XOMAT X-ray film (Kodak) overnight Filter hybridization was performed in duplicate to confirm positive signals. Secondary and tertiary screens were performed until single homogenous clones were isolated.

This isolated genomic clone was then subjected to nucleotide sequence analysis; Nucleotide sequence analysis was performed essentially as described in Example 1, and revealed the sequence of the rat biogenic amine receptor shown in FIG. 2 (SEQ ID No.: 3). The putative protein product of the gene is also shown in FIG. 2 (SEQ ID No: 4). The sequence was found to have an open reading frame comprising 996 nucleotides encoding a protein 332 amino acids in length, and having a predicted molecular weight of about 38 kD kilodaltons prior to post-translational modification. The sequence immediately 5' to the proposed initiation codon was found to contain several translation termination codons in-frame with the open reading frame, supporting the assignment of the translation start site. Predicted transmembrane domains (using the algorithm of Eisenberg et al. (1984, J. Molec. Biol. 179: 125-142)) are boxed and identified by Roman numerals (I-VII), and, two sites of possible N-linked glycosylation are identified in the amino-terminal portion of the protein with solid triangles. A potential protein kinase C site was also found in the C-terminal tail.

The predicted amino acid sequences of the transmembrane domains of the novel biogenic amine receptor were compared with the corresponding sequences in the orphan Neuro Transmitter receptor, orphan GPCR57 and 58, human dopamine D1 receptor, B2 adrenergic receptor, and serotonin 5HT4C receptor, the results of these comparisons are shown in FIG. 3: Amino acid residues that are found in common between the different mammalian biogenic amine receptors are outlined in black. The predicted amino acid sequences of the transmembrane domains were also compared with corresponding sequences m human D1 dopamine receptor, human D2 dopamine receptor, rat serotonin 1c receptor, rat a1-b adrenergic receptor, rat serotonin 4 receptor, rat serotonin 1a receptor, human a-2 adrenergic receptor, and human H-2 histamine receptor (Probst et al., 1992, *DNA Cell Biology* 11: 1-20). Amore detailed comparison of these amino acid sequences are quantified in Table I, showing the percentage extent of homology in pairwise fashion between the different biogenic amine receptors.

TABLE I

| Receptor | % Identity |
|---|---|
| human D1 dopamine | 40 |
| human D2 dopamine | 37 |
| rat α1-b adrenergic | 37 |
| rat serotonin 1c | 35 |
| rat α1 adrenergic | 35 |
| rat serotonin 4 | 35 |
| rat serotonin 1a | 34 |
| human α2 adrenergic | 33 |
| human H-2 histamine | 33 |

Comparisons are made individually at each transmembrane domain (TMI-TMVII), as an average over all transmembrane domains (TM avg) and as the average degree of amino acid sequence homology for each protein as a whole (avg/all). These results support the conclusion that the novel mammalian receptor disclosed herein is a biogenic amine receptor. In addition, the certain amino acid residues in other G-protein coupled receptors (such as Asp$^{103}$ in TM III) were also found in the novel cloned receptor described herein. These data are consistent with the fact that the biogenic amine receptors have a significantly higher homology to the novel receptor disclosed herein than any other members of the G-protein coupled receptor family. The sequence DRY (amino acids 120-123 the human sequence and amino acids 119-122 in the rat sequence) is conserved in them majority of G-protein coupled receptors. Expression of this receptor in a rat insulinoma suggests that biogenic amines may play a role in pancreatic cell function.

The Asp in TMIII is thought to be a counterion to the positively charged amino group present in biogenic amines. In addition, the deduced amino acid sequence predicts a Ser in TMV, which would be able to form a hydrogen bond with the para-hydroxyl group of molecules such as the dopamine, norepinephrine, and epinephrine, as well as the trace amines para-tyramine, octopamine, and synephrine. One Ser was found in the receptor compared with the adrenergic and dopamine receptors, which contain an additional one or two Ser residues N-terminal to the "SerPheTyrXaaPro" (where "Xaa" is any residue) motif in TMV. However, an additional Thr is found directly N-terminal to the Ser that might hydrogen bond with ligands. In TMIV, there is a Irp that is found in the rhodopsin family of G-protein coupled receptors. Distal and two residues proximal to this Tip, the receptor displays significant homology to members of the biogenic amine receptor family. In the C-terminal portion of the deduced TMV sequence there is a Pro residue 6 amino acids N-terminal of the generally conserved Pro residue found in TMIV of biogenic amine receptors. Also, the two Ser residues in TMIV that are conserved among GPCRs activated by biogenic amines are not present in the novel receptor of the invention.

These results support the conclusion that the novel G-protein coupled receptor genes of the invention are biogenic amine receptors.

EXAMPLE 3

Construction of a Recombinant Expression Constructs, DNA Transfection and Functional Expression of the Novel Mammalian Biogenic Amine Receptor In order to biochemically characterize the novel mammalian (rat) biogenic amine receptor described in Example 2, and to confirm that it encodes a novel biogenic amine receptor, the rat cDNA was cloned into a mammalian expression construct (pRcRSVneo, obtained from Invitrogen, San Diego, Calif.), the resulting recombinant expression construct transfected into COS-7 cells (for transient expression assays) and human embryonic kidney cells (HEK293) for stable expression assays, and cell membranes (CQS-7) or cell lines (HEK293) were generated that expressed the receptor protein in cellular membranes at the cell surface. Such cells and membranes isolated from such cells were used for biochemical characterization experiments described below.

The entire coding region of the receptor DNA insert was amplified using PCR as described above with primers specific for flanking sequences; such PCR primers advantageously contained restriction enzyme digestion recognition sites at the 5' termini such that digestion with said restriction enzymes allowed facile cloning of the receptor cDNA into the RcRSVneo mammalian expression construct PCR products generated in this way were subcloned in to the RcRSV vector using conventional techniques (see Sambrook et al., ibid.) and the orientation of the inserted cDNA confirmed by restriction enzyme digestion analysis of insert-containing subclones. Such recombinant expression constructs were introduced into COS-7 cells using the calcium-phosphate precipitation technique (Chen & Okayama, 1987, *Molec. Cell. Biol.* 7: 2745-2752), the transfected cells allowed to express the receptor for between 24-96 hours, and then cell membranes containing the receptor were isolated. Such membranes were harvested from cells grown on 15 cm plates by pelleting the cells at 20,000 rpm in a solution of 50 mM Tris-HCl (pH 7.4). The protein concentration was adjusted to 15-80 μg/sample for each of the binding studies described below.

These recombinant expression constructs were also introduced into HEK293 cells using the calcium-phosphate precipitation technique, and stably-transfected clones were selected by growth in the mammalian neomycin analog G418 (Grand Island Biological Co., Long Island, N.Y.), as the vector RcRSV contains a functional copy of a bacterial neomycin resistance gene. Stable cell lines were then selected for membrane binding studies based on mRNA expression levels of individual neomycin-resistant transfected clones determined by Northern analysis (see Sambrook et al., ibid.). Cell membranes were prepared and used as described above for COS-7 cell transfectants.

Expression of the biogenic amine receptor gene in transfected cells was verified by Northern blot analysis of individual transfectants, performed using conventional techniques. Total cellular was extracted from transfected cells using and RNA Easy kit (obtained from Qiagen, Valencia, Calif.). For Northern hybridization, 10 μg of total cellular RNA was subjected to electrophoresis in a 1.2% agarose gel using HEPES/EDTA buffer (pH 7.8) overnight. The electrophoresed RNA was then transferred to a GeneScreen Plus membrane (New England Nuclear, Boston, Mass.) by capillary transfer, and fixed to the membrane by baking at 85° C. for 1 h. The membrane was then prehybridized overnight at 37° C. in the following buffer: 50% formamide, 1% sodium dodecyl sulfate (SDS), 5×SSC (where 1×SSC is 0.15M NaCl/0.015M sodium citrate, pH 7), 50 μg/mL denatured salmon sperm DNA, and 5× P-buffer (comprising 0.25M Tris, pH 7.5, 0.5% sodium pyrophosphate, 0.5% SDS, 1% bovine serum albumin, 1% polyvinylpyrrolidone and 1% Ficoll (400,000 MW)). After prehybridization, $^{32}$P-labeled DNA prepared from the fill-length genomic receptor clone described above was added at a concentration of $3\times10^6$ cm/mL and the membrane hybridized overnight at 37° C. The hybridized membrane was then washed using the following high-stringency washing conditions: 10 min at room temperature in a wash solution of 2×SSC/1% SDS; 10 min at 60° C. in 2×SSC/1% SDS; and finally 5 min at 60° C. in 0.5×SC, 1%/SDS, where the washing solutions were changed between each washing step. The washed membrane was then exposed overnight to X-ray film QX-omat, Kodak, Rochester, N.Y.).

The results of these experiments are shown in FIG. 4. As shown in the photograph, the transfected biogenic amine receptor is expressed in transfected HEK293 cells.

Specific binding assays using a variety of biogenic amine receptor agonists and antagonists were performed on membranes from both transient and stable transfectants. Ligand binding experiments were performed essentially as described in Bunzow et al. (1988, Nature 336: 783-787). In binding experiments, increasing amounts of membrane protein (from 15-80 μg) was incubated with each of the radioactively-labeled biogenic amine agonist or antagonist to be tested for 120 min at 22° C. in a total volume of mL.

EXAMPLE 4

Distribution of Biogenic Amine Receptor Expression in Mammalian Cell Lines, Rat Brain and Peripheral Tissues The distribution of mRNA corresponding to expression of the biogenic amine receptor gene in various regions of the rat brain was determined by reverse transcription/polymerase chain reaction (RT-PCR) performed as follows. Total RNA from various rat brain sections was isolated using the RNA Easy kit (Qiagen) described in Example 3 and converted to single-stranded cDNA using reverse transcriptase (BRL, Gaithersburg, Md.) primed by oligo dT or random primers or a combination of both these priers. PCR was then performed using the 5' sense primer (TCT CTG AGT GAT GCA TCT ITG; SEQ ID No. 7) corresponding to the 5' extent of the receptor coding sequence and either an antisense primer (AGC AGT GCT CAA CTG TTC TCA CCA TGC; SEQ ID No.: 8) having its 3' end at nucleotide residue 243 of the SEQ ID No. 3 (resulting in a PCR product of about 250 bp in length) or an antisense primer (GCA CGA TTA ATT GAC CTC GCT TG; SEQ ID No.: 9) having its 3' end at nucleotide residue 650 of the SEQ ID No. 3 (resulting in a PCR product of about 650 bp in length). Using either primer pair, PCR was performed for 35 cycles, wherein one cycle consisted of incubations at 94° C. for 90 sec (denaturation), 55° C. for 90 sec (annealing), and 72° C.

for 120 sec (extension). The resulting fragments were resolved from 30 μL reaction mixture using 1% agarose gel electrophoresis and visualized by ethidium bromide staining and UV illumination. The fragments were then transferred onto a nylon membrane (GeneScreen Plus, NEN) by capillary transfer and hybridized under high stringency conditions as described above with a $^{32}$P-labeled probe prepared from the full-length rat genomic clone encoding the novel biogenic amine receptor of the invention as described herein. Hybridized fragments were detected using a phosphoimager (Molecular Devices, Mountain View, Calif.).

Figure 5B:
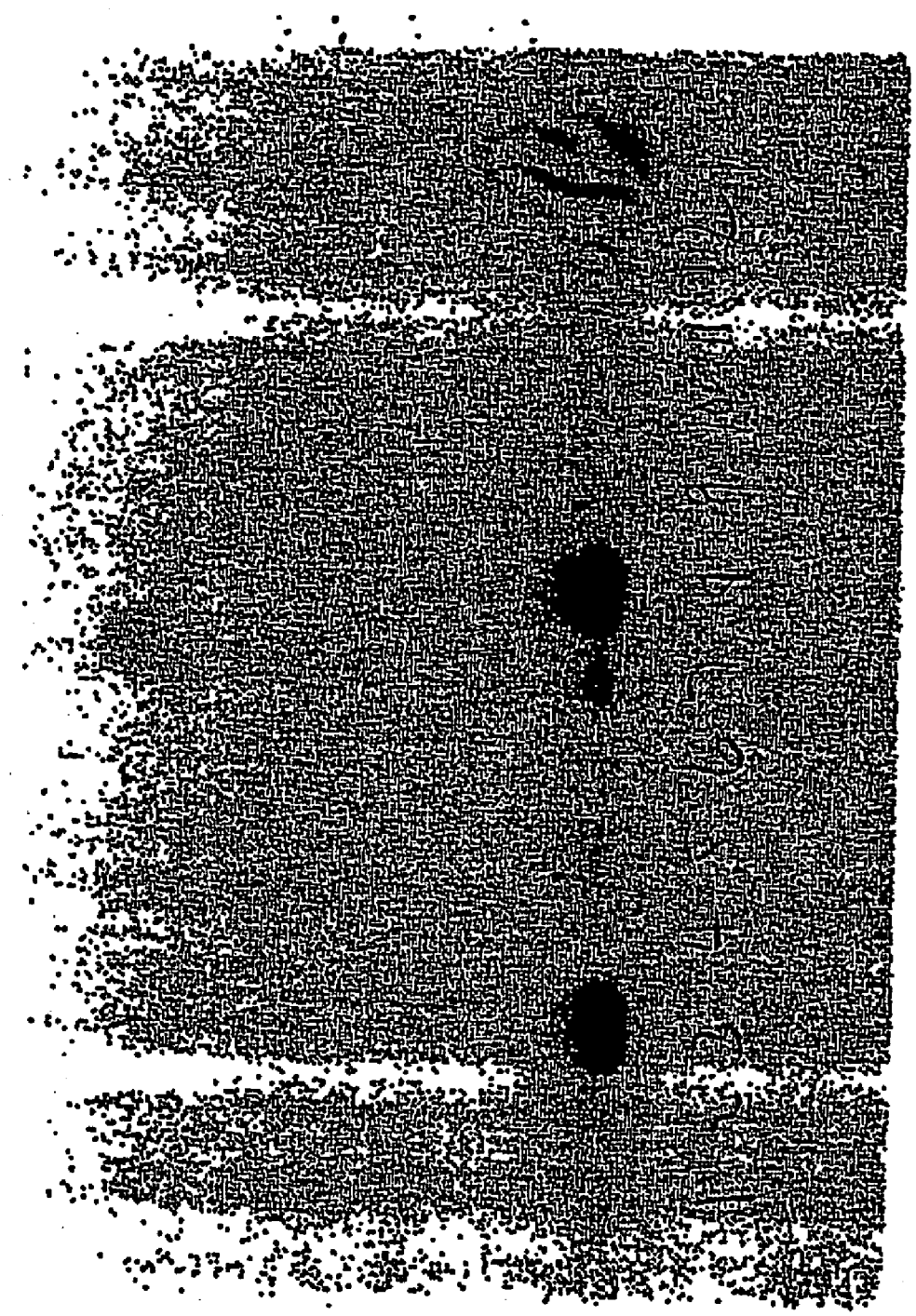
FIG. 5B is an autoradiogram of a nylon membrane containing DNA fragments transferred from the agarose gel shown in FIG. 5A and probed with $^{32}$P-labeled nucleic acid prepared from the coding sequence of the rat genomic clone encoding the rat trace amine receptor of the invention.
Figure 7:
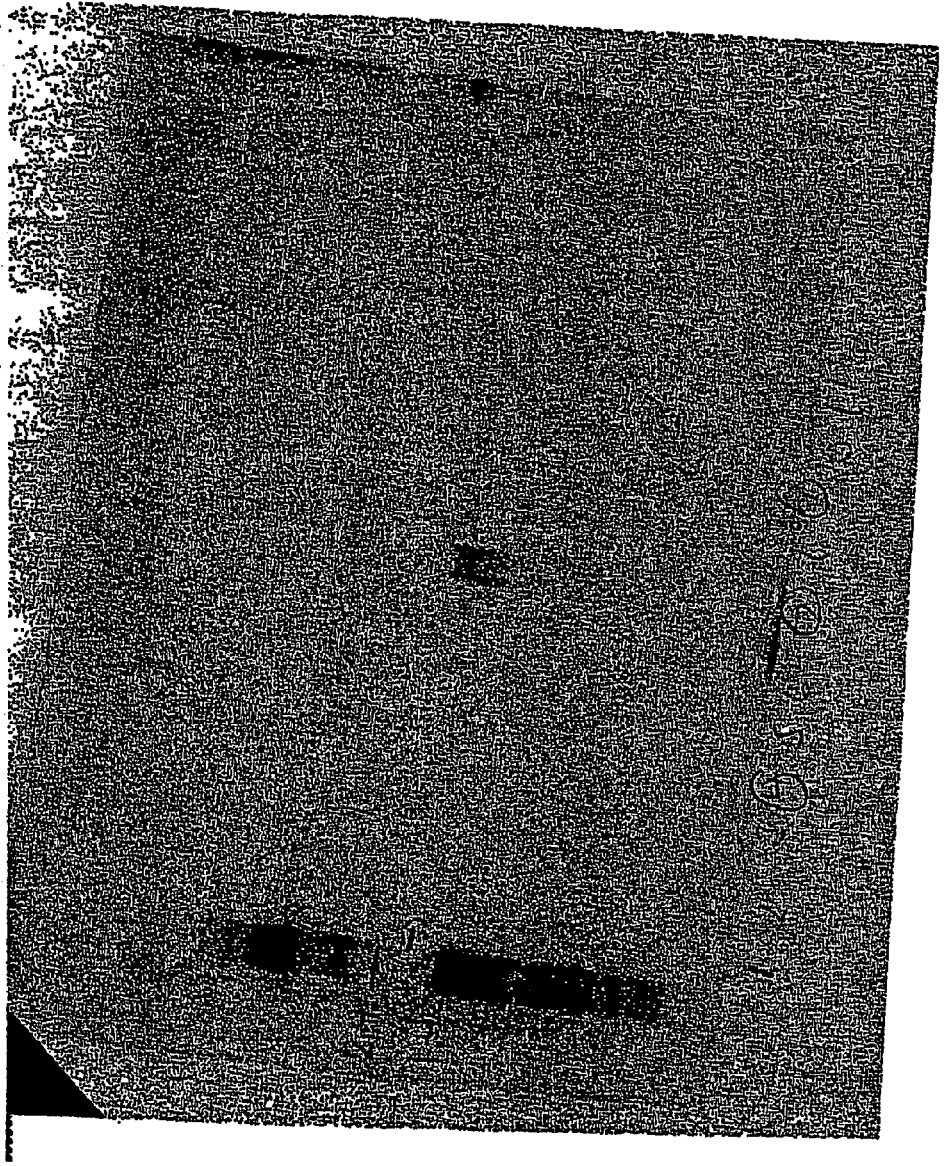
FIG. 7 is a photograph of an autoradiogram of Northern analysis of mRNA expressed in various cell lines expressing a mammalian biogenic amine receptor of the invention after transfection with a recombinant expression construct encoding the rat biogenic amine receptor.

The results of these experiments are shown in FIGS. 5A and 5B. FIG. 5A shows a photograph of an ethidium bromide stained 1% agarose gel viewed under ultraviolet light illumination. PCR product (10 μL of a 30 μL reaction mixture) was electrophoresed as described above, and bands specific for the predicted fragments of the rat biogenic amine receptor of the invention (250 or 650 bp) were detected. FIG. 5B shows the results of the hybridization assay, which results in greater sensitivity of detection of PCR-amplified fragments. These results indicated that the biogenic amine receptor was expressed strongly in midbrain and olfactory tubercle, less strongly in the olfactory bulb, moderately in the striatum and weakly in the hypothalamus.

Northern analysis of total RNA was performed as described in Example 2 above to detect biogenic amine receptor expression in various established mammalian cell lines. These results are shown in FIG. 6. Expression of the biogenic amine receptor gene of the invention was detected only in rat insulinoma cell line RIN5, while the AM42J cell line from which the cloned cDNA was obtained did not show a signal in this experiment, indicating it was present only at low levels and could not be detected in a Northern blot prepared from total cellular RNA (i.e., not having been enriched for mRNA, for example, by selection with oligo (dT)).

Figure 8A:
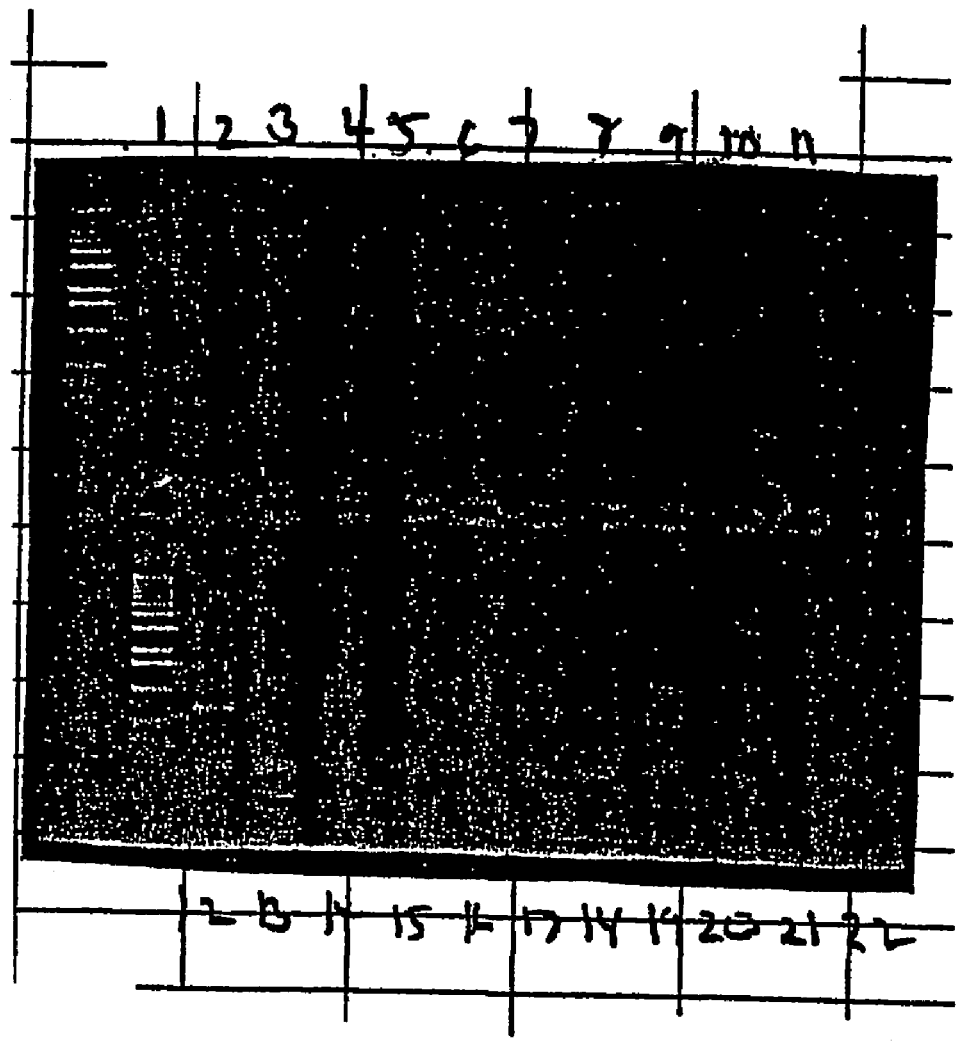
FIG. 8A is a photograph of an ethidium bromide-stained and ultraviolet light irradiated agarose gel containing DNA fragments produced by RT-PCR of RNA from rat tissues. The PCR products resolved on this gel are from the following rat tissues: lane 1, liver (oligo(dT) primed); lane 2, brain (dT); lane 3, spleen (dT); lane 4, lung (dT); lane 5, heart (dT); lane 6, tests (dT); lane 7, kidney (dT); lane 8, intestine (dT); lane 9, COS-7 cell oligo(dT)-selected mRNA from cells transformed with the RC-RSV/rat biogenic amine receptor construct of the invention; lane 10, striatum (dT); lane 11, midbrain (random primed; rp); lane 12, olfactory tubercle (rp); lane 13, cortex (rp+dT); lane 14, midbrain (dT); lane 15, olfactory tubercle (rp); lane 16, olfactory bulb (dT); lane 17, hippocampus (dI); lane 18, midbrain (dT); lane 19, thalamus (dT); lane 20, striatum (dT); lane 21, olfactory bulb (dT); lane 22, water (negative control).

The results of RT-PCR analysis performed on mRNA obtained from various rat tissues as described above are shown in FIG. 8A, and hybridization analysis f these results is shown in FIG. 8B to increase detection of PCR-amplified fragments. The transcript was widely distributed throughout the brain, with the highest levels of expression detected in the olfactory bulb, nucleus accumbens/olfactory tubercle, prefrontal cortex and other cortical regions, midbrain regions consisting of substantia nigra and ventral tegmentum, cerebellum, and pons/medulla. Among peripheral tissues, the highest level was observed in the liver, with lesser expression detected in kidney, gastrointestinal tract, spleen, pancreas, and heart.

These results indicated the following pattern of biogenic amine receptor expression in these tissues:

olfactory tubercle>intestine☐midbrain, cortex,
  spleen>heart, kidney

The receptor was also expressed at detectable levels in lung, transfected COS cells, and olfactory bulb. These results are consistent with known patterns of trace amine receptor expression in olfactory tubercle and midbrain.

EXAMPLE 5

Cloning the Human Trace Amine Receptor Gene

The novel mammalian trace amine receptor cDNA obtained in Example 2 was used to isolate a partial genomic clone from a library of human genomic DNA cloned in lambda EMBL3 (obtained from Clontech, Palo Alto, Calif.) as follows. The full-length rat receptor cDNA (~1 kb in length) was $^{32}$P-labeled by the random priming technique a kit obtained from Stratagene (San Diego, Calif.) according to the manufaetner's instructions. This probe was then used to screen the human genomic library, which had been plated and then transferred to nylon membranes (Gene Screen Plus, NEN, Boston, Mass.). Hybridization was performed in a solution of 50% formamide, 5×SSC, 1% SDS, 5× Denhardt solution, and salmon sperm DNA (50 micrograms/mL) with the radioactive probe at 2×10$^6$ cpm/mL and at a temperature of 37° C. overnight. The nylon filters were then washed at room temperature in a solution of 2×SSC/0.1% SDS for 10 minutes, followed by awash at 55° C. in a solution of 2×SSC/0.1% SDS for 15 minutes, and finally a wash at 55° C. in a solution of 0.5×SSC/0.1% SDS for 5 minutes. Filters were then exposed to XOMAT X-ray film (Kodak) overnight at −80° C. Filter hybridization was performed in duplicate to confirm positive signals. Secondary and tertiary screens were performed until single homogenous clones were identified.

Individual genomic clones were then isolated and the nucleotide sequence determined. The nucleotide sequence analysis, performed essentially as described in Example 1, revealed that the longest insert contained a partial N-terminal sequence of the human homologue of the rat trace amine receptor. Based on this information a set of oligonucleotide primers were synthesized having the following sequence:

Primer VII (sense):
5' TTGACAGCCCTCAGGAATGATG 3' and  (SEQ. ID: NO: 10)

Primer VIII (antisense):
5' ATGGAAAATGGAGGCTGAGCTCAG 3'   (SEQ. ID NO: 11)

These primers were then used to identify a bacterial artificial chromosome (BAC) clone encoding the entire human trace amine receptor gene. Pools of BAC DNA obtained from Research Genetics (Release IV, Catalogue #96011) were subjected to PCR in a 30 micoliter solution that contained primers VII and VIII in addition to 50 nM Tris-HCl (pH 8.3), 2.5 mM MgCl$_2$0.01% gelatin, 250 μM each dNTP, and 2.5 units of Taq polymerase (Saiki et al., 1988, *Science* 239: 487-491). Each PCR amplification cycle consisted of incubations at 94° C. for 90 sec (denaturation), 50° C. for 90 sec (annealing), and 72° C. for 120 sec (extension) for 35 cycles.

Amplified products of the PCR reaction were separated on a 1.0% agarose gel (see Sambrook et al., ibid.). Fragments of the expected size (63.0 bp) were subcloned into the plasmid vector pBluescript (Stratagene, LaJolla, Calif.) and sequence analysis of the inserts confirmed that the BAC contained the human trace amine receptor gene of interest. To obtain the complete DNA sequence of the novel human trace amine receptor gene sense oligonucleotide primers were designed based on the sequence information obtained from the BAC and EMBL3 clones. The resulting sequence information was then used in the design of additional primers. This process was, repeated until the end of the coding region was reached.

Consistent with its rat homologue the novel human trace amine receptor is encoded by a single coding exon. The sequence of the human receptor is presented in FIG. 1. Interestingly, the open reading frame of the human homologue of the trace amine receptor gene is 21 bases longer than the rat (1017 vs 996, respectively) which translates into a human receptor that is 339 amino acids long compared to a receptor of 332 amino acids in the rat (shown in FIG. 2).

A comparison between the primary amino acid sequences of the human and rat receptors is presented in FIG. 3.

EXAMPLE 6

Chromosomal Mapping of the Genomic Locus of the Human Biogenic amine Receptor Gene The chromosomal locus of the human trace amine receptor gene of the invention was mapped by fluorescence in situ hybridization as follows.

BAC DNA encoding the human trace amine receptor described in Example 5 was nick-translated using digoxigenin-11-UTP for use as a probe for in situ chromosomal mapping to localize the gene. This fluorescently labeled DNA was hybridized in situ to denatured human metaphase chromosomes for 16 hours. Signal was detected in the presence of DAPI (4,6-diamidino-2-phenylindole) counter staining and the chromosome was identified by sequential G-banding. The hybridization signal appeared to be consistent with a chromosomal location on the distal long arm of chromosome 6. By alignment of the hybridized metaphases with an ideogram of chromosome 6 (at the 400 band stage), the human trace amine receptor gene was assigned to the locus 6q23.

Figure 9B:
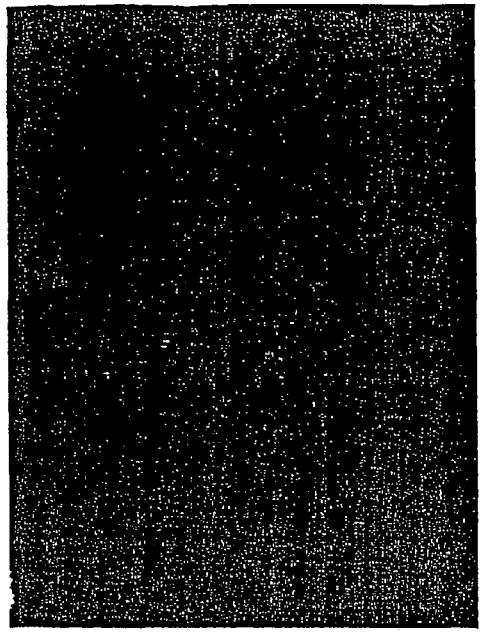
FIGS. 9A through 9D are photographs of fluorescence in situ hybridization analysis of human chromosomes probed with a fluorescently-labeled human artificial chromosome (BAC) containing the human biogenic amine receptor DNA (BAC obtained from Research Genetics, Release IV of DNA pools, Catalog #96001; clone address: plate 278, Row D, Column 22).
Figure 9D:
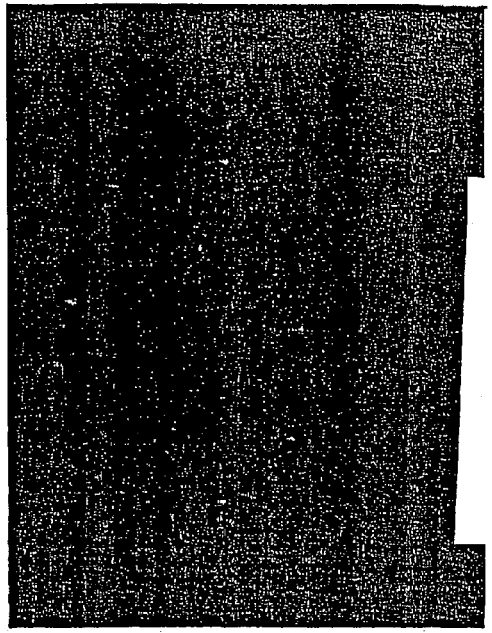
Figure 9A:
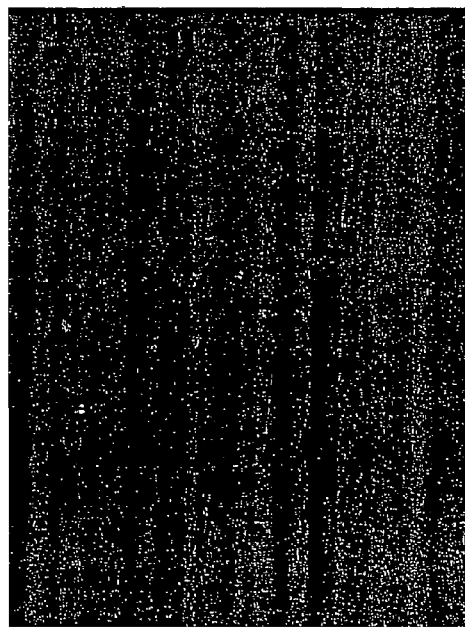
Figure 9C:
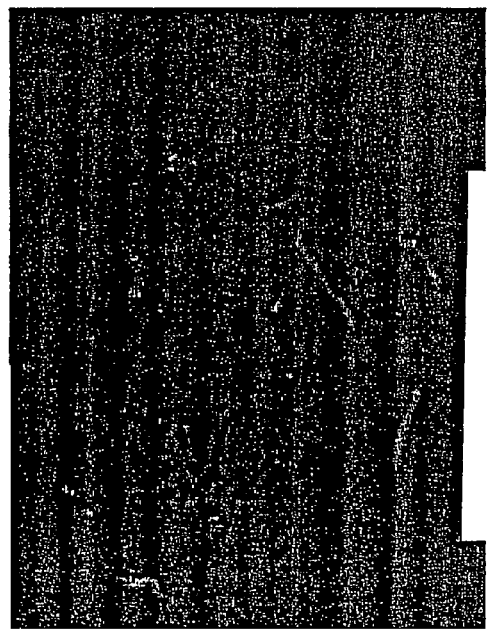
Figure 9E:
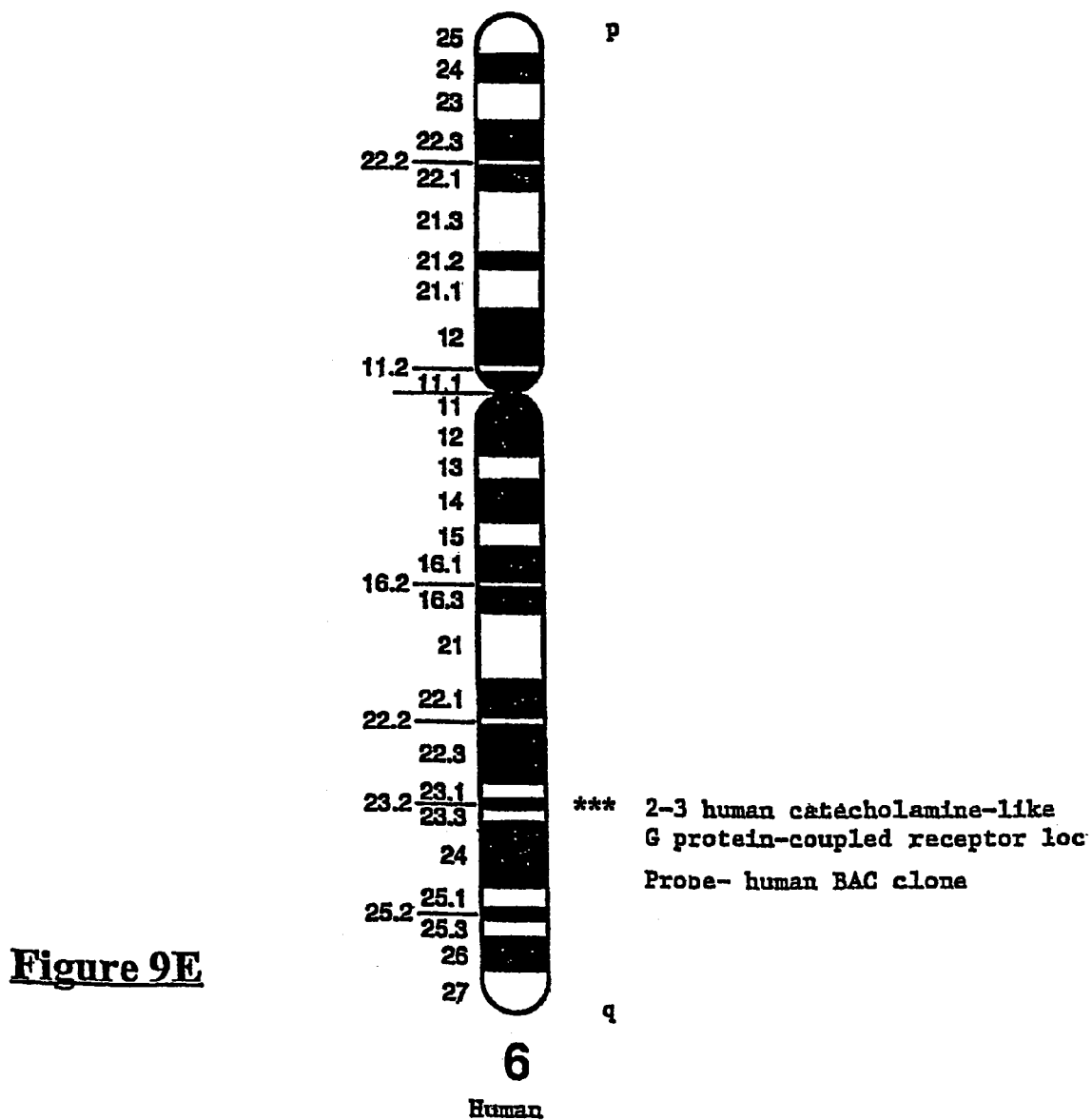
FIG. 9E is a schematic diagram of human chromosome 6 denoting the location of the human biogenic amine locus at 6q23.2.
Figure 10A:
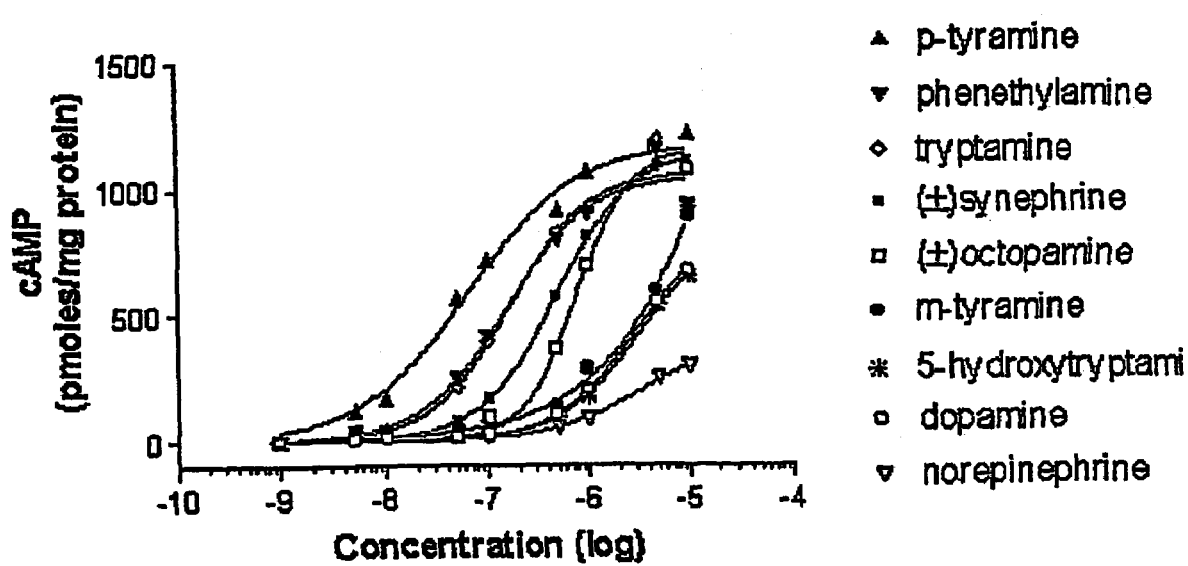
FIG. 10A is a graph showing the ability of various endogenous compounds to stimulate the rat trace amine receptor heterologously expressed in HEK 293 cells in a dose-dependent manner.
Figure 10B:
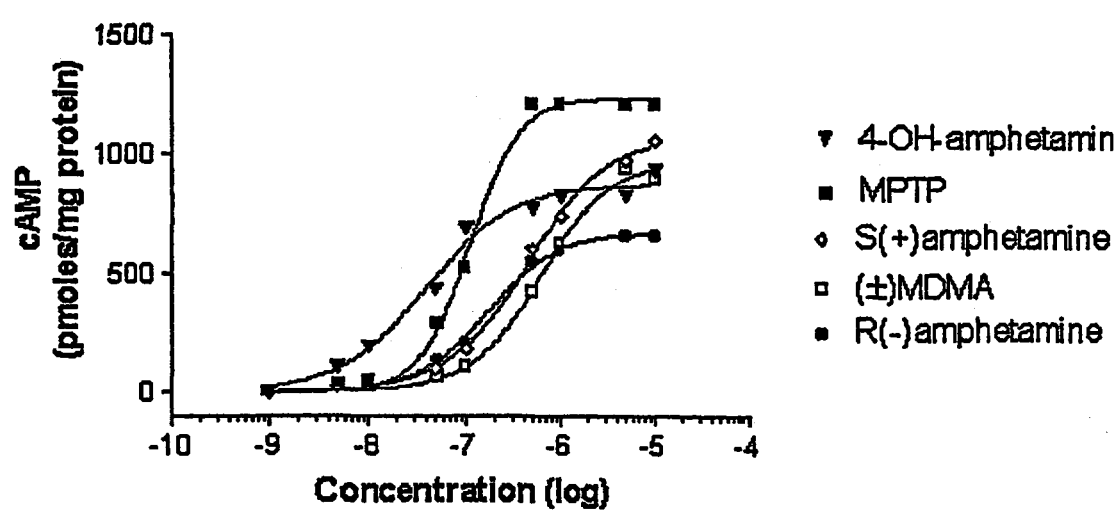
FIG. 10B is a graph showing the ability of various synthetic compounds to stimulate the rat trace amine receptor heterologously expressed in HE 293 cells in a dose-dependent manner.
Figure 11:
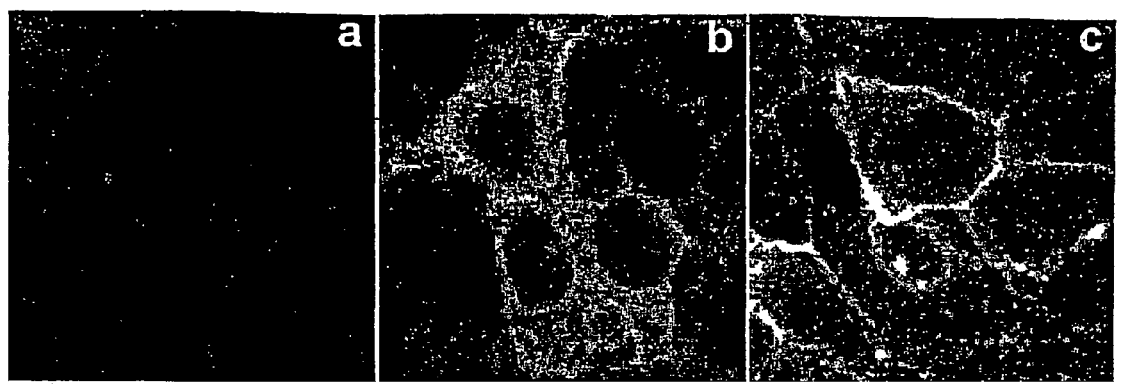
FIGS. 11A through 11C are photographs of immunohistochemical staining of HEK 293 cells expressing epitope-tagged rat trace amine receptor. M1 tagged receptors were bound to anti-FLAG antibodies followed by Cy5 goat anti-mouse IgG in the absence (FIG. 11A) or presence (FIG. 11B) of 0.1% TritonX-100. Control cells shown in FIG. 11C express dopamine D1 receptors and were stained with, antibodies in the presence of Triton X-100.
Figure 12A:
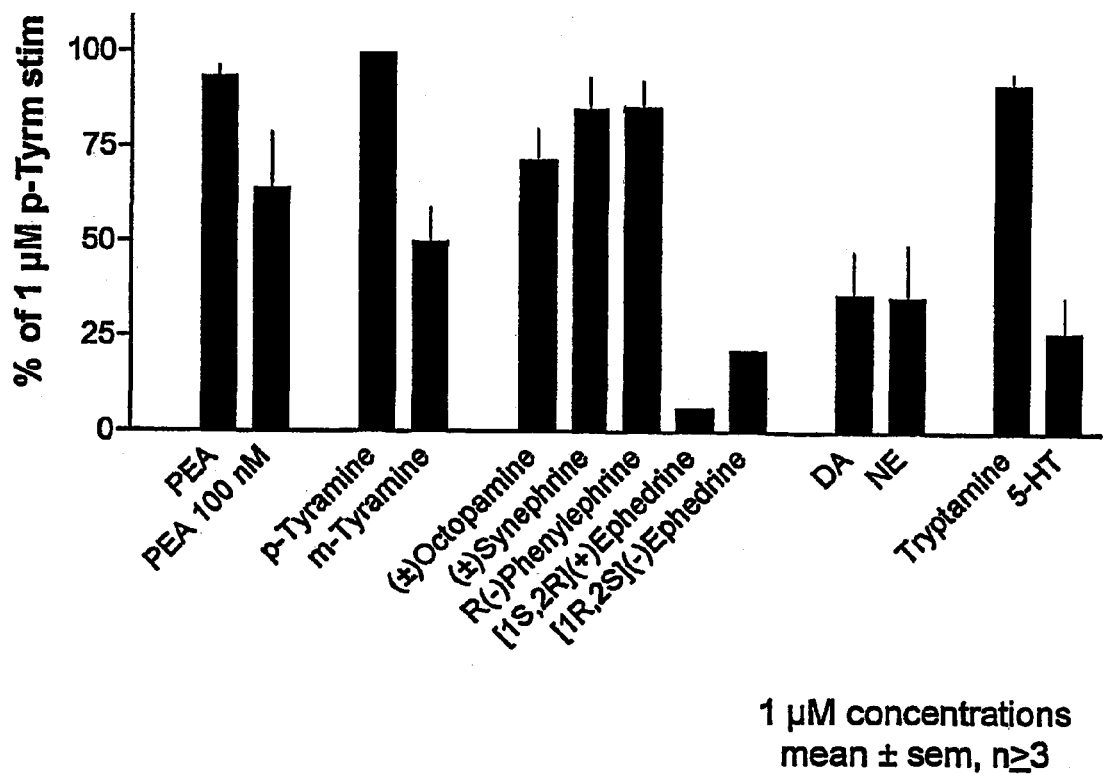
FIGS. 12A through 12G are graphs showing assays of cAMP production in HUEK 293 cells stably transfected with the rat receptor of the invention.
Figure 12B:
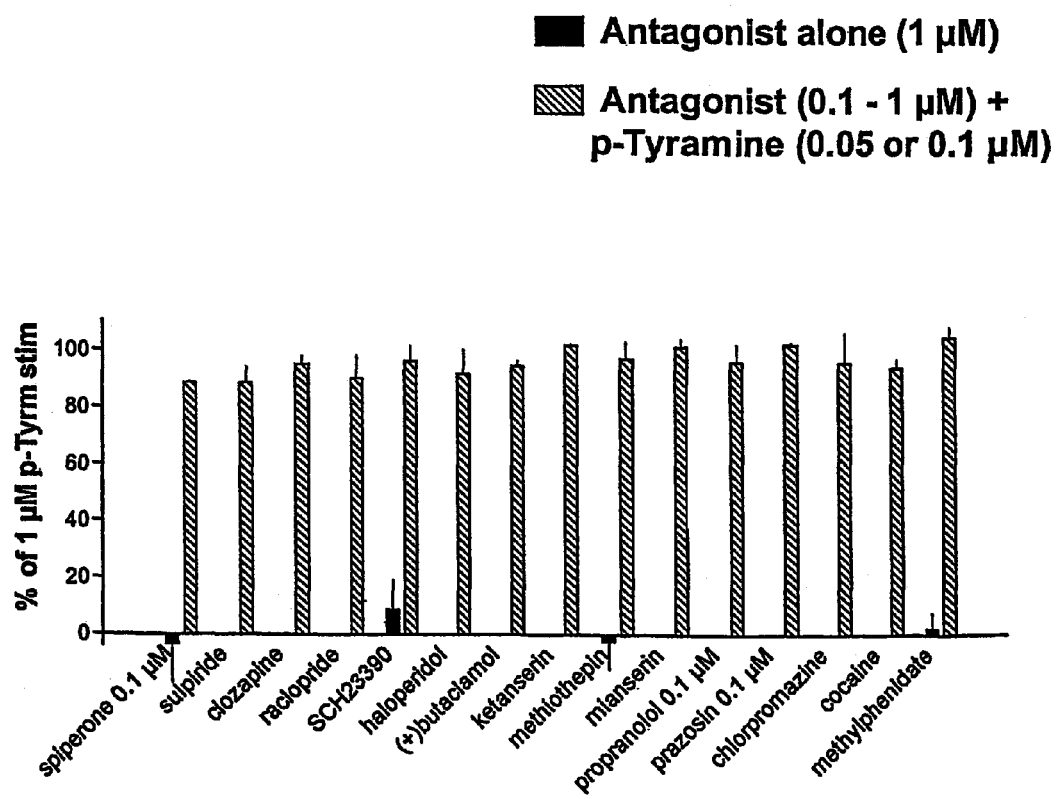
Figure 12C:
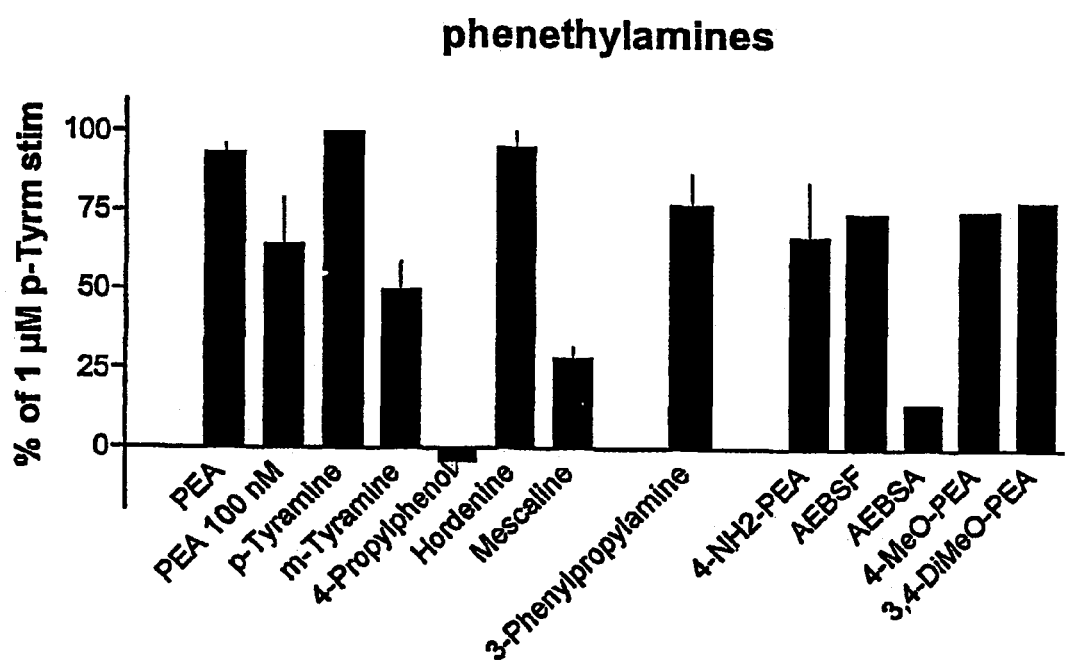
Figure 12D:
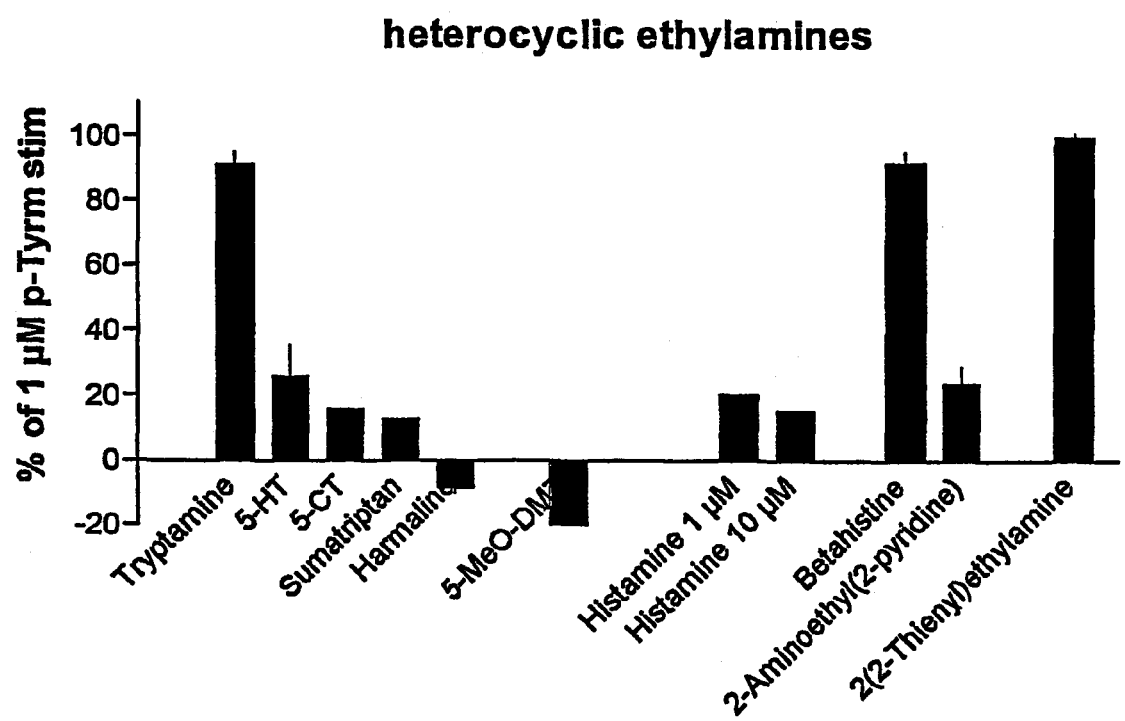
Figure 12E:
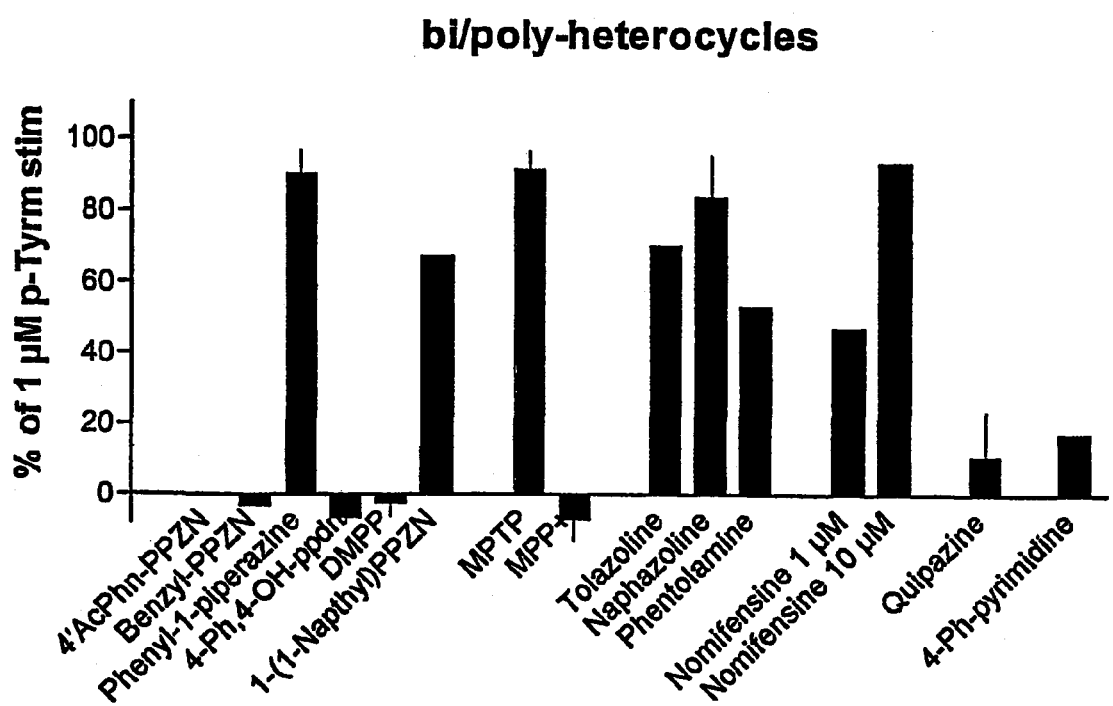
Figure 12F:
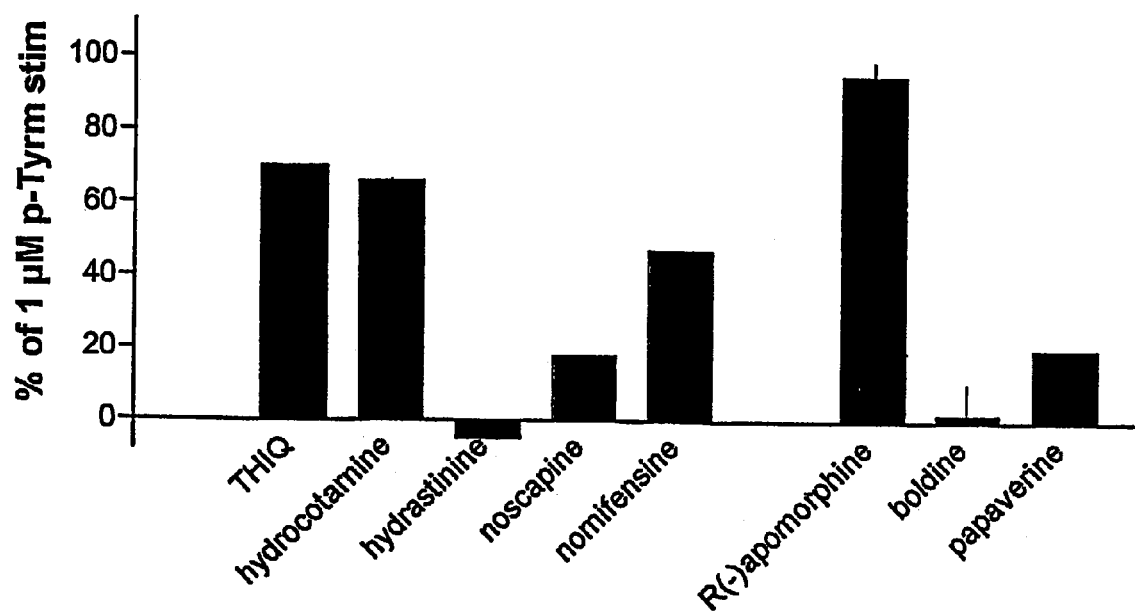
Figure 12G:
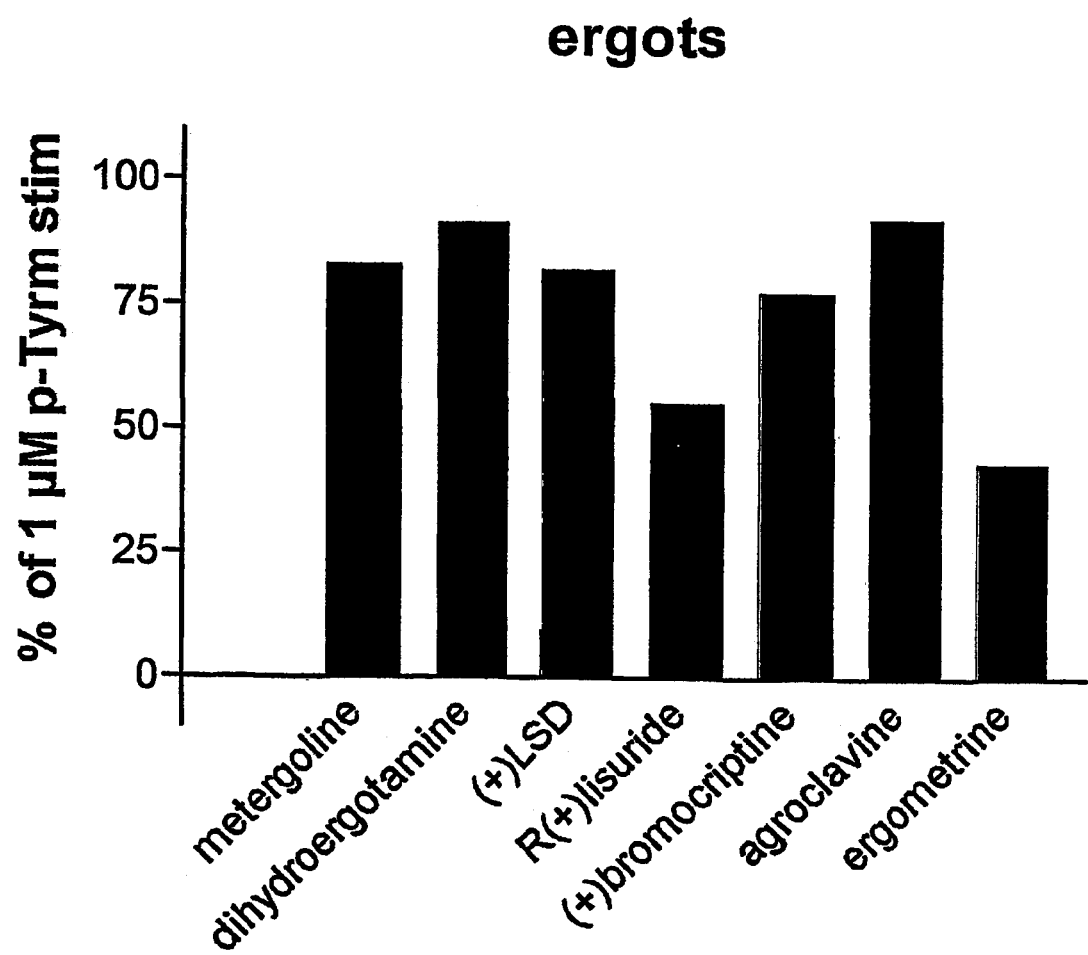

The results of these experiments are shown in FIGS. 9A through 9D, and a schematic representation of these results is shown in FIG. 9E. As can be seen in these Figures, the human trace amine receptor gene corresponding to the cDNA provided by the invention was mapped to human chromosome 6, specifically at 6q23.2.

This chromosomal localization is particularly noteworthy because it is one of the few regions that have been reproducibly associated with schizophrenia in linkage studies (Cao et al., 1997, *Genomics* 43: 1-8; Martinez et al., 1999, *Am J Hum Genet* 88: 337-343; Levinson, et al. 2000, *Am J Hum Genet* 67: 652-663; Mowry and Nancarrow, 2001, *Clin Exp Pharmacol Physiol* 28: 66-69), suggesting the possibility that hTAR1 may be involved in the mechanism of psychosis. The relevance of this receptor to the etiology of psychosis is enhanced by the evidence that 3-MT is a potent and efficacious agonist. 3-MT is the major metabolite of dopamine produced by the enzyme COMT, a variant of which was recently found to be transmitted with greater frequency to schizophrenic offspring in a family based association study (Egan et al., 2001, *Proc Natl Acad Sci USA* 98: 6917-6922).

EXAMPLE 7

Detection of MAP Kinase Pathway Stimulation by the Human Trace Amine Receptor Gene It has been determined that G-protein coupled receptors are capable of stimulating the MAP (microtubule-associated protein) kinase assay in mammalian cells. The recognition of this role of G-protein coupled receptors has facilitated the development of an assay for testing the response of G-protein coupled receptors to potential ligands in vitro, thereby simplifying characterization of said receptors.

In this assay, activation of the pathway by ligand binding to receptor results in increased phosphorylation of mammalian transcription factor Elk by the MK kinase. The phosphorylated Elk transcription factor then binds to promoters containing cis-sequences responsive to this transcription factor. Transcription factor binding results in increase transcription of sequences operatively linked and under the transcriptional control of such Elk-responsive promoters. Most advantageously, reporter genes, such as β-galactosidase or firefly luciferase are operatively linked to such Elk-responsive promoters, thereby permitting ligand binding to a receptor to be linked with expression of the reporter gene.

HEK 293 cells were transfected with the full-length human clone encoding the trace amine receptor of the invention contained in the pcDNA 3.1 expression vector (Invitrogen), wherein the first 22 nucleotides of the 5' untranslated region is followed by an initiation codon (ATG, Met), followed by nucleotides encoding an 8-amino acid FLAG sequence (Asp-Tyr-Lys-Asp-Asp-Asp-Asp-Lys; SEQ ID No.: 12), followed by a nucleotide sequence encoding the 21 amino acids of the human D2 receptor (as disclosed in co-owned U.S. Pat. No. 5,880,260, issued Mar. 9, 1999, incorporated by reference in its entirety herein) that follow the Met initiation codon in the native D2 sequence, which is followed by the complete sequence of the human trace amine receptor; this construct was termed H2-3 pcDNA3.1.

Control cells were transfected with pcDNA3.1 without the rat trace amine receptor sequences. All cells were also co-transfected with 2 additional constructs: one (elk-gal) that encoded the yeast transcription factor gal under the transcriptional control of an Elk-responsive promoter, and another encoding firefly luciferase under the transcriptional control of a gal-responsive promoter. In cells containing the rat trace amine-encoding construct, ligand binding to the receptor expressed thereby activated the map kinase (MK) pathway, which results in phosphorylation of the endogenous Elk transcription factor. In its phosphorylated state, Elk interacts with the elk DNA binding site and leads to activation of transcription of the gal gene contained in the elk-gal plasmid. In turn, transcription of the luciferase gene is activated in the co-transfected luciferase construct. Luciferase transcription was quantified using a luminometer, and gave an indirect measure of MK activation by each ligand. The results of these experiments as shown in Table II, showing the fold stimulation for each potential ligand compared with cells incubated in the absence of the ligand.

TABLE II

| Ligand | H2-3 pcDNA3.1 | pcDNA3.1 |
|---|---|---|
| Dopamine | 1.21 | 1.04 |
| Serotonin | 1.22 | 1 |
| Norepinephrine | 1.69 | 1.3 |
| Clonidine[1] | 1.47 | 1.07 |
| SKF82958[2] | 2.52 | 0.79 |
| ADTN67[3] | 1.93 | 0.78 |
| Quinpirole[3] | 2.14 | 0.6 |

[1]$\alpha_2$-adrenergic and imidazoline receptor agonist
[2]D1 dopamine receptor agonist
[3]α-2 adrenergic receptor agonist These results indicate that the cloned rat genomic DNA disclosed herein encodes a receptors that is specifically activated by drugs that target certain biogenic amine receptors. However, the profile for this activation does not correspond to that for any of the known biogenic amine receptors, indicating that this is a novel, brain-specific, biogenic amine-binding receptor having a unique pharmacology useful thereby as a therapeutic target.

EXAMPLE 8

Cellular Localization of the Novel Trace Amine Receptor

Enhanced expression of the receptor was achieved by cloning the full-length rat cDNA into the mammalian expression vector pcDNA3.1/V5/His-TOPO (Invitrogen). A PCR product was generated that upon expression produced the rat receptor sequence preceded at its amino terminus by a cleavable 16 amino acid signal sequence of the influenza hemaglutinin virus immediately followed by the 8 amino acid M1-Flag epitope and then a two amino acid linker (MetGly) just before the initiation methionine (Guan et al., 1992, *J Biol Chem.* 267:21995-21998).

HEK293 cells were transfected using the Lipofectamine transfection reagent and cells stably expressing the construct were selected in G418. The flag-tagged receptor was analyzed by immunofluorescence to determine cellular localization. For comparison, localization of the D1 receptor in BEK293 cells stably expressing the cloned flag-tagged human D1 receptor was also examined. Cells were maintained in DM media containing 10% fetal calf serum and 700 μg/mL G418 (Life Technologies, Bethesda, Md.). Confluent cells were detached with PBS solution contaning 0.05% trypsin and 0.53 mM EDTA, harvested, diluted 1:10, and plated on glass microscope coverslips coated with poly-D-lysine and grown at 37° C. for 48 hours. Cells were washed twice with PBS and fixed with 2.5% paraformaldehyde in PBS for 20 minutes. Cells were then incubated for 30 minutes with anti-FLAG monoclonal antibody (1:500; Sigma) in blocking buffer solution (3% dry milk 1 mM $CaCl_2$, 50 mM Tris HCl Ph 7.5) with or without 0.1% Triton X-100. After 3 washes with Tris-buffered saline containing 1 mM $CaCa_2$, cells were incubated for 30 minutes with goat anti-mouse IgG conjugated to Cy5 (Jackson Immuno Research Laboratories, Inc., West Grove, Pa.) diluted 1:200 in blocking solution. Cells were washed three times and mounted onto microscope slides with Mowiol® (Aldrich, Milwaukee, Wis.) and analyzed by confocal microscopy using an MRC-1000 laser scanning confocal imaging system (Bio-Rad Laboratories, Richmond, Calif.) equipped with an Optiphot II Nikon microscope and a Plan Apo 60×1.4 oil immersion objective. In the absence of Triton X-100, little staining was observed in the cells for the receptor. In the presence of Triton X-100, which permeablizes the cell membrane, the receptor showed pronounced staining in the cytoplasm accompanied by some staining in the plasma membrane. As expected, the D1 receptors were found primarily on the plasma membrane.

EXAMPLE 9

Stimulation of the Novel Receptor in Stably Transfected HEK293 Cells in Response to Various Endogenous and Synthetic Compounds HEK293 cells stably transfected with the pcDNA3.1/V5/His-TOPO expression vector containing the full-length rat cDNA clone described above were assayed for cAMP production in response to various ligands.

In the performance of these assays, HEK293 cells were harvested in Krebs-Ringer buffer (KRH; Sigma) and preincubated in KRH with 200 μm EBMX. For drug treatments, cells were incubated in KRH with 100 μM IBMX with the test compound (or 10 μM forskolin) for 1 hour at 37° C. The cells were then boiled for 20 min after adding an equal volume of 0.5 mM sodium acetate buffer, centrifuged to remove cell debris, and the resulting extract was analyzed for cAMP content using competitive binding of $^3$H-cAMP to a cAMP binding protein (Diagnostic Products Corp., Los Angeles, Calif.). Data were normalized according to protein content as determined using the Bradford reagent (Bio-Rad, Richmond, Calif.). Concentration-response curves were plotted and $EC_{50}$'s calculated with GraphPad Prism software (San Diego, Calif.).

Using this assay, levels of cAMP stimulation in response to 1 μM concentrations of test compounds were measured and levels were normalized to the levels of cAMP elicited by 1 μM p-tyramine. The results of the cAMP assays are show in FIGS. 12A through 12G and are summarized in the following Tables. Table III shows the potencies and efficacies of compounds stimulating the receptor. Drugs that are strong, medium, and weak stimulators of the receptor are listed in Table IV and neurotransmitter's that are stimulators of the receptor are listed in Table V. Compounds that demonstrate strong responses have affinities and/or efficacies that are comparable or higher than those of p-tyramine. Compounds that display weak stimulation of cAMP are either inactive or antagonists. Medium stimulators illicit a response less than the strong stimulators but greater than the weak stimulators.

TABLE III

| | $EC_{50}$ (nM ± SEM) | Maximal Stimulation* (% ± SEM) |
|---|---|---|
| Neurotransmitters | | |
| p-tyramine | 69 ± 9 | 100 |
| Phenethylamine | 237 ± 71 | 76 ± 16 |
| Tryptamine | 309 ± 76 | 90 ± 6 |
| Synephrine | 584 ± 100 | 90 ± 2 |
| Octopamine | 1298 ± 350 | 102 ± 3 |
| m-tyramine | 5375 ± 1184 | 74 ± 3 |
| Dopamine | 5920 ± 2639 | 48 ± 5 |
| 5-hydroxytryptamine | 12800 ± 4181 | 47 ± 9 |
| Drugs | | |
| 4-hydroxyamphetamine | 51 ± 12 | 79 ± 2 |
| MPTP | 99 ± 11 | 93 ± 7 |
| R-amphetamine | 209 ± 44 | 48 ± 7 |
| S-amphetamine | 440 ± 10 | 84 ± 3 |
| MDMA | 1749 ± 1152 | 65 ± 13 |

*Values are expressed as percent of stimulation by p-tyramine

| NEUROTRANSMITTERS | | | DRUGS | |
|---|---|---|---|---|
| | EC50 (nM) | | | EC50 (nM) |
| P-tyramine | 44.9 | 82 | R-OH amphetamine | 11.3 |
| Phenylethylamine | 218 | 124 | p-tyramine | 20.2 |
| Tryptamine | 248.4 | 519 | S-amphetamine | 64.2 |
| Octopamine | 873.5 | 1400 | R-amphetamine | 108 |
| Dopamine | 4818.0 | 4000 | MDMA | 179 |
| Serotonin | 1913.0 | 8000 | S-methamphetamine | 188 |
| m-tyramine | 7189.0 | 5800 | R-methamphetamine | 236 |
| Synephrine | ND | — | p-methoxy PEA | 346 |
| Noradrenaline | 0 | — | | |

TABLE IV

DRUGS

| STRONG STIMULATOR | MEDIUM STIMULATOR | WEAK STIMULATOR |
|---|---|---|
| 4-OH amphetamine | Phentolamine | N-phenylephrine |
| S-amphetamine | 3-phenylpropylamine | Clonidine |
| R-amphetamine | Ergotmetrine | Quinpirole |
| S-methamphetamine | R-ephedrine | Quipazine |
| R-methamphetamine | Tolazoline | 4-benzylpiperidine |
| MDMA | Prenylamine | |
| p-chloroamphetamine | Mescaline | |
| Betahistine | p-methoxy-PEA | |
| 4-NH-PEA | 3,4 dimethoxy PEA | |
| 2-thiophenylethylamine | Reboxetine | |
| 1-phenylpiporazine | AEBSF | |
| Phenylephrine | Hydrocotarnomine | |
| Apomorphine | Bromocriptine | |
| metergoline | 6,7 ADTN | |

TABLE V

NEUROTRANSMITTERS

| STRONG STIMULATOR | MEDIUM STIMULATOR | NO STIMULATION |
|---|---|---|
| p-tyramine | Dopamine | norepinephrine |
| Phenylethylamine | Serotonin | |
| Tryptamine | m-tyramine | |
| Octopamine | | |
| Synephrine | | |

In summary, these molecules had $EC_{50}$s in the following rank order (lowest to highest):

p-tyramine<β-PEA<tryptamine<synephrine<octopamine<meta-tyramine (m-tyramine)≦dopamine<5-HT<<norepinephrine, epinephrine.

The rank order of potencies observed for the human trace amine receptor indicates that a hydroxyl group at the meta position on β-PEA analogs or at the 5-position on tryptamine has deleterious effects on agonist potency, a trend that is contrary to that observed for catecholamine receptors. Comparison of the amino acid sequence of the trace amine receptor with those of catecholamine and 5-HT receptors suggests a structural basis for this change in selectivity. It has been proposed from mutagenesis studies of the $β_2$-AR and the $5\text{-HT}_{1A}$ receptor (Ho et al., 1992, FEBS Lett 301: 303-306) that serine residues in transmembrane domain V contribute to the binding affinity of agonists, and that $Ser^{5.42}$ and/or $Ser^{5.43}$ form a hydrogen bond network with the catecholamine meta-hydroxyl groups (Liapalas et al. 2000, J Biol Chem 275: 37779-37788). The Ser residue in position 5.42 is conserved in every catecholamine receptor. Curiously, the corresponding residues in the mammalian trace amine receptor of the invention are instead Ala5.42 and $Phe^{5.43}$ 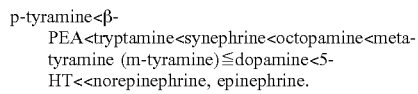 (FIG. 1) whereas the more deeply positioned $Ser^{5.47}$, proposed to interact with the para-hydroxyl group, is found in the instant receptors and in the catecholamine receptors alike (Liapakis et al., ibid.). The absence of Ser residues in positions 5.42 and 5.43 of rTAR1 diminishes the potencies of phenethylamine agonists that have meta-hydroxyl groups (e.g. catecholamines, m-tyramine) as compared to those that do not.

Another trend observed in the pharmacological survey also differentiates the instant trace amine receptor from known biogenic amine receptors and, furthermore, may hint at a physiological role of the receptor. The meta-O-methyl metabolites of the catecholamines-3-methoxytyramine (3-methyldopamine), 3-methoxy-β-4-dihydroxy-β-phenethylamine (normetanephrine); and 3-methoxy-β-4-dihydroxy-N-methyl-β-phenethylamine (metanephrine)—are efficacious activators of the trace amine receptor of the invention, and are significantly more potent than their precursors dopamine, norepinephrine, and epinephrine (FIG. 3B). This finding is unusual because at other known catecholamine receptors, these meta-O-methyl metabolites generated by catechol-O-methyltransferase have vastly diminished affinities and/or intrinsic efficacies as compared with their parent catecholamines (Langer and Rubio, 1973, Naunyn Schmiedeberg's Arch Pharmacol 276: 71-88; Seeman, 1980, Pharmacol Rev 32:230-313). The data disclosed herein indicated that increasing lipophilicity of catechonine meta-substituents by O-methylation actually increases their affinity for the trace amine receptors of the invention. These data are consistent with the finding of Liapakis et al. (ibid.) that replacement of $Ser^{5.42}$ in the $β_2$-AR with Ala or Val residues decreased the affinities of β-PEA analogs containing meta-hydroxyl groups but increased the potencies of analogs lacking them. Accordingly, endogenous agonists of the trace amine receptors of the invention may include some "inactive" catecholamine metabolites such as 3-methoxytyramine, the principal extracellular metabolite of dopamine (Wood and Altar, 1988, Pharmacol Rev 40: 163-187). It is important to note that 3-methoxy4-hydroxyphenylacetic acid (homovanillic acid), the oxidized metabolite of 3-methotyramine lacking the amine group, displayed no detectable activity towards the trace amine receptors of the invention. The tissues that contain the highest levels of mRNA encoding a trace amine receptor of the invention were the same tissues known to express high levels of catechol-O-methyltransferase—liver, kidney, gastrointestinal tract and brain (reviewed in Mânnistö and Kaakkola, 1999, Pharmacol Rev 51: 593-628).

Surprisingly, the trance amine receptor is more potently activated by the presumably "inactive" catecholamine metabolites 3-methoxytramine (3-MT), normetanephrine and metanephrine than by the neurotransmitters dopamine, norepinephrine, and epinephrine themselves.

Given the structural similarity of amphetamine to P-PEA and p-tyramine, it was of obvious interest to determine whether amphetamine analogs including methamphetamine and its congener MDMA ("ecstasy") could activate the trace amine receptors of the invention. These and several other amphetamine analogs potently stimulated cAMP production in recombinant cells expressing this receptor. Amphetamines act directly on the receptor, since these drugs (at 1 μM concentrations) produced no cAMP stimulation in control cells transfected either with an empty vector or with the human D1 receptor. Amphetamine analogs that activate the receptor include both classic neurotransmitter transporter substrates as well as a prototypical hallucinogenic amphetamine, 2-amino,(1-[2,5-dimethoxy-4-iodophenyl]propane, which has poor affinity for transporters but high affinity for $5\text{-HT}_2$ receptors (Marek and Aghajaniian, 1998, ibid.). Some structural modifications of amphetamine significantly changed their potencies at the receptor: p-OH-amphetamine (α-methyl-p-tyramine), the major amphetamine metabolite (Cho and Kumagai, 1994, in Amphetamine and Its Analogs: Psychopharmacology, Toxicology, and Abuse (Cho A K and Segal D S eds), Academic Press: San Diego, pp 43-77), proved to be the most potent agonist of the trace amine receptor of the invention yet identified. In contrast, two N-ethyl analogs, (±)fenfluramine and (±)N-ethylamphetamine, had substantially lower activities than the N-methyl congeners, methamphetamine and MDMA or than the primary amine congeners.

The ability of tryptamine to activate the rTAR1 suggested that some ergot alkaloids might act as agonists. A variety of widely used ergot alkaloids and ergoline derivatives, including ergometrine, dihydroergotamine, D-LSD, and the antiparkinsonian agents bromocriptine and lisuride, potently activate the trace amine receptor. Recognition that this receptor is involved in the biological response to these compounds increases the ability to elucidate their complex in vivo pharmacology.

Antagonists of biogenic amine receptors and transporters were also found to stimulate camp production in recombinant cells expressing the trace amine receptors of the invention. Such compounds include the adrenergic antagonists phentolamine and tolazoline, the serotonergic antagonists cyproheptadine, dihydroergotsmnine, and metergoline, and the nonsubstrate inhibitors of dopamine transporter protein nomifensine and 1-methyl 4phenyl-1,2,3,6-tetrahydropyridine. The antipsychotic drug chlorpromazine, typically considered to be a dopamine receptor-antagonist, also acted as a weak agonist with the trace amine receptors of this invention. None of the biogenic amine receptor antagonists tested were able to antagonize trace amine receptor binding or activity when coincubated (at 1 or 10 μM concentrations) with $EC_{50}$ concentrations of β-PEA or p-tyramine (data not shown). Although the trace amine receptor of this invention displayed a broad ligand selectivity when expressed in HEK293 cells, it is not activated by many compounds including acetylcholine, nicotine, GABA, glutamate, morphine (data not shown) and histamine.

It should be understood that the foregoing disclosure emphasizes certain specific embodiments of the invention and that all modifications or alternatives equivalent thereto are within the spirit and scope of the invention as set forth in the appended claims.

What we claim is:

1. An isolated nucleic acid comprising a nucleotide sequence encoding the biogenic amine cell surface receptor set forth as SEQ ID NO: 4.

2. A nucleic acid according to claim 1 wherein the biogenic amine receptor is a trace amine receptor.

3. A recombinant expression construct comprising a nucleic acid having a nucleotide sequence encoding the biogenic amine cell surface receptor according to claim 1, wherein the construct is capable of expressing the receptor in a transformed culture of eukaryotic or prokaryotic cells.

4. A recombinant expression construct according to claim 3 wherein the construct is optimized for expression in a prokaryotic cell.

5. A cell culture transformed with the recombinant expression construct of claim 3, wherein the transformed cell culture expresses the biogenic amine cell surface receptor.

6. A cell culture transformed with the recombinant expression construct of claim 3, wherein the transformed cell culture expresses the biogenic amine cell surface receptor.

7. An isolated nucleic acid hybridization probe comprising a nucleotide sequence encoding the amino acid sequence of SEQ ID NO: 4.

8. An isolated nucleic acid comprising a nucleotide sequence encoding a human or rat trace amine receptor that hybridizes to the full-length complement of a nucleic acid having a nucleotide sequence encoding the amino acid sequence of SEQ ID NO: 4, under conditions of 37° C. in a buffer comprising 50% formamide, 1% sodium dodecyl sulfate, 5×SSC, 50 µ/mL denatured salmon sperm DNA, and 5× P-buffer comprising 0.25M Tris, pH 7.5, 0.5% sodium pyrophosphate, 0.5% SDS, 1% bovine serum albumin, 1% polyvinylpyrrolidone and 1% Ficoll, wherein said trace amine receptor encoded by said nucleotide sequence is capable of binding a trace amine, when said receptor is expressed by a cell.

9. An isolated nucleic acid according to claim 8, wherein the nucleic acid hybridizes to the full-length complement of a nucleic acid having a nucleotide sequence encoding the amino acid sequence of SEQ ID NO: 4, under washing conditions of 10 minutes at room temperature in a wash solution of 2×SSC/1% SDS, followed by 10 min at 60° C. in 2×SSC/1% SDS, followed by 5 min at 60° C. in 0.5× SSC/1% SDS.

* * * * *

SEQUENCE LISTING

```
<160> NUMBER OF SEQ ID NOS: 12

<210> SEQ ID NO 1
<211> LENGTH: 1125
<212> TYPE: DNA
<213> ORGANISM: Homo Sapiens
<220> FEATURE:
<221> NAME/KEY: CDS
<222> LOCATION: (21)..(1037)

<400> SEQUENCE: 1
ctaattgaca gccctcagga atg atg ccc ttt tgc cac aat ata att aat att        53
                      Met Met Pro Phe Cys His Asn Ile Ile Asn Ile
                        1               5                      10 tcc tgt gtg aaa aac aac tgg tca aat gat gtc cgt gct tcc ctg tac        101
Ser Cys Val Lys Asn Asn Trp Ser Asn Asp Val Arg Ala Ser Leu Tyr
             15                  20                  25 agt tta atg gtg ctc ata att ctg acc aca ctc gtt ggc aat ctg ata        149
Ser Leu Met Val Leu Ile Ile Leu Thr Thr Leu Val Gly Asn Leu Ile
         30                  35                  40 gtt att gtt tct ata tca cac ttc aaa caa ctt cat acc cca aca aat        197
Val Ile Val Ser Ile Ser His Phe Lys Gln Leu His Thr Pro Thr Asn
     45                  50                  55 tgg ctc att cat tcc atg gcc act gtg gac ttt ctt ctg ggg tgt ctg        245
Trp Leu Ile His Ser Met Ala Thr Val Asp Phe Leu Leu Gly Cys Leu
 60                  65                  70                  75 gtc atg cct tac agt atg gtg aga tct gct gag cac tgt tgg tat ttt        293
Val Met Pro Tyr Ser Met Val Arg Ser Ala Glu His Cys Trp Tyr Phe
                 80                  85                  90 gga gaa gtc ttc tgt aaa att cac aca agc acc gac att atg ctg agc        341
Gly Glu Val Phe Cys Lys Ile His Thr Ser Thr Asp Ile Met Leu Ser
             95                 100                 105 tca gcc tcc att ttc cat ttg tct ttc atc tcc att gac cgc tac tat        389
Ser Ala Ser Ile Phe His Leu Ser Phe Ile Ser Ile Asp Arg Tyr Tyr
        110                 115                 120 gct gtg tgt gat cca ctg aga tat aaa gcc aag atg aat atc ttg gtt        437
Ala Val Cys Asp Pro Leu Arg Tyr Lys Ala Lys Met Asn Ile Leu Val
    125                 130                 135 att tgt gtg atg atc ttc att agt tgg agt gtc cct gct gtt ttt gca        485
Ile Cys Val Met Ile Phe Ile Ser Trp Ser Val Pro Ala Val Phe Ala
140                 145                 150                 155 ttt gga atg atc ttt ctg gag cta aac ttc aaa ggc gct gaa gag ata        533
Phe Gly Met Ile Phe Leu Glu Leu Asn Phe Lys Gly Ala Glu Glu Ile
                160                 165                 170
```

```
tat tac aaa cat gtt cac tgc aga gga ggt tgc ctc gtc ttc ttt agc      581
Tyr Tyr Lys His Val His Cys Arg Gly Gly Cys Leu Val Phe Phe Ser
        175                 180                 185 aaa ata tct ggg gta ctg acc ttt atg act tct ttt tat ata cct gga      629
Lys Ile Ser Gly Val Leu Thr Phe Met Thr Ser Phe Tyr Ile Pro Gly
    190                 195                 200 tct att atg tta tgt gtc tat tac aga ata tat ctt atc gct aaa gaa      677
Ser Ile Met Leu Cys Val Tyr Tyr Arg Ile Tyr Leu Ile Ala Lys Glu
205                 210                 215 cag gca aga tta att agt gat gcc aat cag aag ctc caa att gga ttg      725
Gln Ala Arg Leu Ile Ser Asp Ala Asn Gln Lys Leu Gln Ile Gly Leu
220                 225                 230                 235 gaa atg aaa aat gga att tca caa agc aaa gaa agg aaa gct gtg aag      773
Glu Met Lys Asn Gly Ile Ser Gln Ser Lys Glu Arg Lys Ala Val Lys
            240                 245                 250 aca ttg ggg att gtg atg gga gtt ttc cta ata tgc tgg tgc cct ttc      821
Thr Leu Gly Ile Val Met Gly Val Phe Leu Ile Cys Trp Cys Pro Phe
                255                 260                 265 ttt atc tgt aca gtc atg gac cct ttt ctt cac tca att att cca cct      869
Phe Ile Cys Thr Val Met Asp Pro Phe Leu His Ser Ile Ile Pro Pro
                    270                 275                 280 act ttg aat gat gta ttg att tgg ttt ggc tac ttg aac tct aca ttt      917
Thr Leu Asn Asp Val Leu Ile Trp Phe Gly Tyr Leu Asn Ser Thr Phe
285                 290                 295 aat cca atg gtt tat gca ttt ttc tat cct tgg ttt aga aaa gca ctg      965
Asn Pro Met Val Tyr Ala Phe Phe Tyr Pro Trp Phe Arg Lys Ala Leu
300                 305                 310                 315 aag atg atg ctg ttt ggt aaa att ttc caa aaa gat tca tcc agg tgt     1013
Lys Met Met Leu Phe Gly Lys Ile Phe Gln Lys Asp Ser Ser Arg Cys
                320                 325                 330 aaa tta ttt ttg gaa ttg agt tca tagaattatt atattttact gttttgcaaa    1067
Lys Leu Phe Leu Glu Leu Ser Ser
                335 tcggttgatg atcatattta tgaacacaac ataacgaacc acatgcacca accacatg     1125

<210> SEQ ID NO 2
<211> LENGTH: 339
<212> TYPE: PRT
<213> ORGANISM: Homo Sapiens

<400> SEQUENCE: 2

Met Met Pro Phe Cys His Asn Ile Ile Asn Ile Ser Cys Val Lys Asn
1               5                   10                  15

Asn Trp Ser Asn Asp Val Arg Ala Ser Leu Tyr Ser Leu Met Val Leu
            20                  25                  30

Ile Ile Leu Thr Thr Leu Val Gly Asn Leu Ile Val Ile Val Ser Ile
        35                  40                  45

Ser His Phe Lys Gln Leu His Thr Pro Thr Asn Trp Leu Ile His Ser
    50                  55                  60

Met Ala Thr Val Asp Phe Leu Leu Gly Cys Leu Val Met Pro Tyr Ser
65                  70                  75                  80

Met Val Arg Ser Ala Glu His Cys Trp Tyr Phe Gly Glu Val Phe Cys
                85                  90                  95

Lys Ile His Thr Ser Thr Asp Ile Met Leu Ser Ser Ala Ser Ile Phe
            100                 105                 110

His Leu Ser Phe Ile Ser Ile Asp Arg Tyr Tyr Ala Val Cys Asp Pro
        115                 120                 125

Leu Arg Tyr Lys Ala Lys Met Asn Ile Leu Val Ile Cys Val Met Ile
```

```
            130                 135                 140
Phe Ile Ser Trp Ser Val Pro Ala Val Phe Ala Phe Gly Met Ile Phe
145                 150                 155                 160

Leu Glu Leu Asn Phe Lys Gly Ala Glu Ile Tyr Tyr Lys His Val
                165                 170                 175

His Cys Arg Gly Gly Cys Leu Val Phe Phe Ser Lys Ile Ser Gly Val
            180                 185                 190

Leu Thr Phe Met Thr Ser Phe Tyr Ile Pro Gly Ser Ile Met Leu Cys
            195                 200                 205

Val Tyr Tyr Arg Ile Tyr Leu Ile Ala Lys Glu Gln Ala Arg Leu Ile
210                 215                 220

Ser Asp Ala Asn Gln Lys Leu Gln Ile Gly Leu Glu Met Lys Asn Gly
225                 230                 235                 240

Ile Ser Gln Ser Lys Glu Arg Lys Ala Val Lys Thr Leu Gly Ile Val
                245                 250                 255

Met Gly Val Phe Leu Ile Cys Trp Cys Pro Phe Phe Ile Cys Thr Val
            260                 265                 270

Met Asp Pro Phe Leu His Ser Ile Ile Pro Pro Thr Leu Asn Asp Val
            275                 280                 285

Leu Ile Trp Phe Gly Tyr Leu Asn Ser Thr Phe Asn Pro Met Val Tyr
290                 295                 300

Ala Phe Phe Tyr Pro Trp Phe Arg Lys Ala Leu Lys Met Met Leu Phe
305                 310                 315                 320

Gly Lys Ile Phe Gln Lys Asp Ser Ser Arg Cys Lys Leu Phe Leu Glu
                325                 330                 335

Leu Ser Ser

<210> SEQ ID NO 3
<211> LENGTH: 999
<212> TYPE: DNA
<213> ORGANISM: Rattus norvegicus
<220> FEATURE:
<221> NAME/KEY: CDS
<222> LOCATION: (1)..(996)

<400> SEQUENCE: 3 atg cat ctt tgc cac aat agc gcg aat att tcc cac acg aac agg aac      48
Met His Leu Cys His Asn Ser Ala Asn Ile Ser His Thr Asn Arg Asn
1               5                   10                  15 tgg tca agg gat gtc cgt gct tca ctg tac agc tta ata tca ctc ata      96
Trp Ser Arg Asp Val Arg Ala Ser Leu Tyr Ser Leu Ile Ser Leu Ile
            20                  25                  30 att cta acc act ctg gtt ggc aac tta ata gta atc att tcg ata tcc     144
Ile Leu Thr Thr Leu Val Gly Asn Leu Ile Val Ile Ile Ser Ile Ser
        35                  40                  45 cac ttc aag caa att cac acg ccc aca aat tgg ctc ctt cat tcc atg     192
His Phe Lys Gln Ile His Thr Pro Thr Asn Trp Leu Leu His Ser Met
    50                  55                  60 gcc gtt gtc gac ttt ctg ctg ggc tgt ctg gtc atg ccc tac agc atg     240
Ala Val Val Asp Phe Leu Leu Gly Cys Leu Val Met Pro Tyr Ser Met
65                  70                  75                  80 gtg aga aca gtt gag cac tgc tgg tac ttt ggg gaa ctc ttc tgc aaa     288
Val Arg Thr Val Glu His Cys Trp Tyr Phe Gly Glu Leu Phe Cys Lys
                85                  90                  95 ctt cac acc agc act gat atc atg ctg agc tcg gca tcc att ctc cac     336
Leu His Thr Ser Thr Asp Ile Met Leu Ser Ser Ala Ser Ile Leu His
            100                 105                 110
```

| | | | | | | | | | | | | | | | | |
|---|---|---|---|---|---|---|---|---|---|---|---|---|---|---|---|---|
| cta | gcc | ttc | att | tcc | att | gac | cgc | tac | tat | gct | gtg | tgc | gac | cct | tta | 384 |
| Leu | Ala | Phe | Ile | Ser | Ile | Asp | Arg | Tyr | Tyr | Ala | Val | Cys | Asp | Pro | Leu | |
| | | | 115 | | | | 120 | | | | 125 | | | | | |
| aga | tac | aaa | gcc | aag | atc | aat | ctc | gcc | gcc | att | ttt | gtg | atg | atc | ctc | 432 |
| Arg | Tyr | Lys | Ala | Lys | Ile | Asn | Leu | Ala | Ala | Ile | Phe | Val | Met | Ile | Leu | |
| | 130 | | | | | 135 | | | | | 140 | | | | | |
| att | agc | tgg | agc | ctt | cct | gct | gtt | ttt | gca | ttt | ggg | atg | atc | ttc | ctg | 480 |
| Ile | Ser | Trp | Ser | Leu | Pro | Ala | Val | Phe | Ala | Phe | Gly | Met | Ile | Phe | Leu | |
| 145 | | | | | 150 | | | | | 155 | | | | | 160 | |
| gag | ctg | aac | tta | gaa | gga | gtt | gag | gag | cag | tat | cac | aat | cag | gtc | ttc | 528 |
| Glu | Leu | Asn | Leu | Glu | Gly | Val | Glu | Glu | Gln | Tyr | His | Asn | Gln | Val | Phe | |
| | | | | 165 | | | | | 170 | | | | | 175 | | |
| tgc | ctg | cgc | ggc | tgt | ttt | cta | ttc | ttc | agt | aaa | gta | tct | ggg | gta | ctg | 576 |
| Cys | Leu | Arg | Gly | Cys | Phe | Leu | Phe | Phe | Ser | Lys | Val | Ser | Gly | Val | Leu | |
| | | | 180 | | | | | 185 | | | | | 190 | | | |
| gca | ttc | atg | acg | tct | ttc | tat | ata | cct | ggg | tct | gtt | atg | tta | ttt | gtt | 624 |
| Ala | Phe | Met | Thr | Ser | Phe | Tyr | Ile | Pro | Gly | Ser | Val | Met | Leu | Phe | Val | |
| | | 195 | | | | | 200 | | | | | 205 | | | | |
| tac | tat | gag | ata | tat | ttc | ata | gct | aaa | gga | caa | gcg | agg | tca | att | aat | 672 |
| Tyr | Tyr | Glu | Ile | Tyr | Phe | Ile | Ala | Lys | Gly | Gln | Ala | Arg | Ser | Ile | Asn | |
| | 210 | | | | | 215 | | | | | 220 | | | | | |
| cgt | gca | aac | ctt | caa | gtt | gga | ttg | gaa | ggg | gaa | agc | aga | gcg | cca | caa | 720 |
| Arg | Ala | Asn | Leu | Gln | Val | Gly | Leu | Glu | Gly | Glu | Ser | Arg | Ala | Pro | Gln | |
| 225 | | | | | 230 | | | | | 235 | | | | | 240 | |
| agc | aag | gaa | aca | aaa | gcc | gcg | aaa | acc | tta | ggg | atc | atg | gtg | ggc | gtt | 768 |
| Ser | Lys | Glu | Thr | Lys | Ala | Ala | Lys | Thr | Leu | Gly | Ile | Met | Val | Gly | Val | |
| | | | | 245 | | | | | 250 | | | | | 255 | | |
| ttc | ctc | ctg | tgc | tgg | tgc | ccg | ttc | ttt | ttc | tgc | atg | gtc | ctg | gac | cct | 816 |
| Phe | Leu | Leu | Cys | Trp | Cys | Pro | Phe | Phe | Phe | Cys | Met | Val | Leu | Asp | Pro | |
| | | | 260 | | | | | 265 | | | | | 270 | | | |
| ttc | ctg | ggc | tat | gtt | atc | cca | ccc | act | ctg | aat | gac | aca | ctg | aat | tgg | 864 |
| Phe | Leu | Gly | Tyr | Val | Ile | Pro | Pro | Thr | Leu | Asn | Asp | Thr | Leu | Asn | Trp | |
| | | 275 | | | | | 280 | | | | | 285 | | | | |
| ttc | ggg | tac | ctg | aac | tct | gcc | ttc | aac | ccg | atg | gtt | tat | gcc | ttt | ttc | 912 |
| Phe | Gly | Tyr | Leu | Asn | Ser | Ala | Phe | Asn | Pro | Met | Val | Tyr | Ala | Phe | Phe | |
| | 290 | | | | | 295 | | | | | 300 | | | | | |
| tat | ccc | tgg | ttc | aga | aga | gcg | ttg | aag | atg | gtt | ctc | ttc | ggt | aaa | att | 960 |
| Tyr | Pro | Trp | Phe | Arg | Arg | Ala | Leu | Lys | Met | Val | Leu | Phe | Gly | Lys | Ile | |
| 305 | | | | | 310 | | | | | 315 | | | | | 320 | |
| ttc | caa | aaa | gat | tca | tct | agg | tct | aag | tta | ttt | ttg | taa | | | | 999 |
| Phe | Gln | Lys | Asp | Ser | Ser | Arg | Ser | Lys | Leu | Phe | Leu | | | | | |
| | | | | 325 | | | | | 330 | | | | | | | |

<210> SEQ ID NO 4
<211> LENGTH: 332
<212> TYPE: PRT
<213> ORGANISM: Rattus norvegicus

<400> SEQUENCE: 4

Met His Leu Cys His Asn Ser Ala Asn Ile Ser His Thr Asn Arg Asn
1               5                   10                  15

Trp Ser Arg Asp Val Arg Ala Ser Leu Tyr Ser Leu Ile Ser Leu Ile
                20                  25                  30

Ile Leu Thr Thr Leu Val Gly Asn Leu Ile Val Ile Ile Ser Ile Ser
            35                  40                  45

His Phe Lys Gln Ile His Thr Pro Thr Asn Trp Leu Leu His Ser Met
        50                  55                  60

Ala Val Val Asp Phe Leu Leu Gly Cys Leu Val Met Pro Tyr Ser Met
65                  70                  75                  80

```
Val Arg Thr Val Glu His Cys Trp Tyr Phe Gly Leu Phe Cys Lys
                85                  90                  95

Leu His Thr Ser Thr Asp Ile Met Leu Ser Ser Ala Ser Ile Leu His
            100                 105                 110

Leu Ala Phe Ile Ser Ile Asp Arg Tyr Tyr Ala Val Cys Asp Pro Leu
        115                 120                 125

Arg Tyr Lys Ala Lys Ile Asn Leu Ala Ala Ile Phe Val Met Ile Leu
    130                 135                 140

Ile Ser Trp Ser Leu Pro Ala Val Phe Ala Phe Gly Met Ile Phe Leu
145                 150                 155                 160

Glu Leu Asn Leu Glu Gly Val Glu Glu Gln Tyr His Asn Gln Val Phe
                165                 170                 175

Cys Leu Arg Gly Cys Phe Leu Phe Phe Ser Lys Val Ser Gly Val Leu
            180                 185                 190

Ala Phe Met Thr Ser Phe Tyr Ile Pro Gly Ser Val Met Leu Phe Val
        195                 200                 205

Tyr Tyr Glu Ile Tyr Phe Ile Ala Lys Gly Gln Ala Arg Ser Ile Asn
    210                 215                 220

Arg Ala Asn Leu Gln Val Gly Leu Glu Gly Ser Arg Ala Pro Gln
225                 230                 235                 240

Ser Lys Glu Thr Lys Ala Ala Lys Thr Leu Gly Ile Met Val Gly Val
                245                 250                 255

Phe Leu Leu Cys Trp Cys Pro Phe Phe Phe Cys Met Val Leu Asp Pro
            260                 265                 270

Phe Leu Gly Tyr Val Ile Pro Pro Thr Leu Asn Asp Thr Leu Asn Trp
        275                 280                 285

Phe Gly Tyr Leu Asn Ser Ala Phe Asn Pro Met Val Tyr Ala Phe Phe
    290                 295                 300

Tyr Pro Trp Phe Arg Arg Ala Leu Lys Met Val Leu Phe Gly Lys Ile
305                 310                 315                 320

Phe Gln Lys Asp Ser Ser Arg Ser Lys Leu Phe Leu
                325                 330

<210> SEQ ID NO 5
<211> LENGTH: 35
<212> TYPE: DNA
<213> ORGANISM: Artificial
<220> FEATURE:
<223> OTHER INFORMATION: oligonucleotide primer
<220> FEATURE:
<221> NAME/KEY: modified_base
<222> LOCATION: (23)..(24)
<223> OTHER INFORMATION: a is inosine

<400> SEQUENCE: 5
gagtcgacct gtgygysaty rcaatkgacm gstac                              35

<210> SEQ ID NO 6
<211> LENGTH: 33
<212> TYPE: DNA
<213> ORGANISM: Artificial
<220> FEATURE:
<223> OTHER INFORMATION: oligonucleotide primer
<220> FEATURE:
<221> NAME/KEY: modified_base
<222> LOCATION: (18)..(18)
<223> OTHER INFORMATION: a is inosine
<220> FEATURE:
<221> NAME/KEY: modified_base
<222> LOCATION: (27)..(27)
<223> OTHER INFORMATION: a is inosine
```

-continued

```
<400> SEQUENCE: 6
cagaattcag wagggcaacc agcagaasry gaa                              33

<210> SEQ ID NO 7
<211> LENGTH: 21
<212> TYPE: DNA
<213> ORGANISM: Artificial
<220> FEATURE:
<223> OTHER INFORMATION: oligonucleotide primer

<400> SEQUENCE: 7
tctctgagtg atgcatcttt g                                           21

<210> SEQ ID NO 8
<211> LENGTH: 27
<212> TYPE: DNA
<213> ORGANISM: Artificial
<220> FEATURE:
<223> OTHER INFORMATION: oligonucleotide primer

<400> SEQUENCE: 8
agcagtgctc aactgttctc accatgc                                     27

<210> SEQ ID NO 9
<211> LENGTH: 23
<212> TYPE: DNA
<213> ORGANISM: Artificial
<220> FEATURE:
<223> OTHER INFORMATION: oligonucleotide primer

<400> SEQUENCE: 9
gcacgattaa ttgacctcgc ttg                                         23

<210> SEQ ID NO 10
<211> LENGTH: 22
<212> TYPE: DNA
<213> ORGANISM: Artificial
<220> FEATURE:
<223> OTHER INFORMATION: oligonucleotide primer

<400> SEQUENCE: 10
ttgacagccc tcaggaatga tg                                          22

<210> SEQ ID NO 11
<211> LENGTH: 24
<212> TYPE: DNA
<213> ORGANISM: Artificial
<220> FEATURE:
<223> OTHER INFORMATION: oligonucleotide primer

<400> SEQUENCE: 11
atggaaaatg gaggctgagc tcag                                        24

<210> SEQ ID NO 12
<211> LENGTH: 8
<212> TYPE: PRT
<213> ORGANISM: Artificial
<220> FEATURE:
<223> OTHER INFORMATION: FLAG sequence

<400> SEQUENCE: 12

Asp Tyr Lys Asp Asp Asp Asp Lys
1               5
```